United States Patent
You et al.

(10) Patent No.: US 9,611,281 B2
(45) Date of Patent: Apr. 4, 2017

(54) BODIPY DERIVATIVES AND METHODS OF SYNTHESIS AND USE THEREOF

(71) Applicant: The Board of Regents of the University of Oklahoma, Norman, OK (US)

(72) Inventors: Youngjae You, Edmond, OK (US); Samuel Awuah, Oklahoma City, OK (US); Ryan Watley, Pine Bluff, AR (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 53 days.

(21) Appl. No.: 14/562,323

(22) Filed: Dec. 5, 2014

(65) Prior Publication Data

US 2015/0158888 A1    Jun. 11, 2015

Related U.S. Application Data

(60) Provisional application No. 61/912,251, filed on Dec. 5, 2013.

(51) Int. Cl.
C07F 5/02    (2006.01)

(52) U.S. Cl.
CPC ................... *C07F 5/022* (2013.01)

(58) Field of Classification Search
CPC ....................................... C07F 5/022
See application file for complete search history.

(56) References Cited

FOREIGN PATENT DOCUMENTS

CN          103183697 A      7/2013

OTHER PUBLICATIONS

Umezawa, et al. Document No. 150:425015, entered in STN Feb. 12, 2009; retrieved from CAPLUS.*
Awuah, Samuel, et al.;"Boron Dipyrromethene (BODIPY)-based photsensitizers for photodynamic therapy"; RSC Advances; 2012, vol. 2, pp. 11169-11183. Published on Sep. 7, 2012.
Awuah, Samuel, et al.; "Theieno-Pyrrole-Fused BODIPY Intermediate as a Platform to Multifunctional NIR Agents"; Chemistry an Asian Journal; 2013, vol. 8, pp. 3123-3132 and pp. S1-S15 of Supporting Information; published online Aug. 27, 2013.
Bandi, Venugopal, et al.; "Thieno-Pyrrole-Fused 4, 4-Difluoro-4-bora-3a, 4a-diaza-s-indacene-Fullerene Dyads: Utilization of Near-Infrared Sensitizers for Ultrafast Charge Separation in Donor—Acceptor Systems"; Journal of the American Chemical Society, 2014, vol. 136, pp. 7571-7574; published May 10, 2014.
Kamkaew, Anyanee, et al.; "BODIPY dyes in photodynamic therapy"; Chem Soc Rev; 2013, vol. 42, pp. 77-88; published on Sep. 26, 2012.
Loudet, Aurore, et al., "BODIPY Dyes and Their Derivatives: Syntheses and Spectroscopic Properties"; Chemical Reviews; 2007, vol. 107, No. 11; pp. 4891-4932, published online Oct. 9, 2007.
Awauah, Samuel G., et al.; "Singlet Oxygen Generation by Novel NIR BODIPY Dyes"; Organic Letters 2011, vol. 13, No. 15; pp. 3884-3887 and pp. 1-17 of Supplementary Information; published online May 25, 2011.

* cited by examiner

*Primary Examiner* — Shawquia Jackson
(74) *Attorney, Agent, or Firm* — Dunlap Codding, P.C.

(57) ABSTRACT

Derivatives of BODIPY (boron dipyrromethene difluoride) and their synthesis and use are disclosed.

20 Claims, 13 Drawing Sheets
(13 of 13 Drawing Sheet(s) Filed in Color)

Untreated           12 hrs after treatment

Untreated      Day 1 post PDT      Day 20 post PDT

Untreated          9hrs post PDT

BODIPY DERIVATIVES AND METHODS OF SYNTHESIS AND USE THEREOF

CROSS-REFERENCE TO RELATED APPLICATIONS/INCORPORATION BY REFERENCE STATEMENT

This application claims priority and benefit under 35 USC §119(e) of U.S. Provisional Application Ser. No. 61/912,251, filed Dec. 5, 2013, the entirety of which is hereby expressly incorporated herein by reference.

BACKGROUND

Photodynamic therapy (PDT) and fluorescence imaging are non-invasive modalities for disease treatment and diagnosis, respectively. Both modalities require the use of a dye (light harvesting material) and light or source of excitation. A sensitizer is used in the case of PDT, while a fluorophore is used in the case of fluorescence imaging. The search for novel non-invasive regimen/agents using tissue penetrable light (e.g., at 600 nm-900 nm) to improve disease prognosis and therapy is expanding due to its advantages of reduced toxicity by avoiding non-ionized species, relatively low cost, and real time monitoring. In general, near infra-red (NIR) fluorescent probes and photosensitizers (PSs) for photodynamic diagnosis and therapy (PDD/PDT), respectively, are more effective than visible ones in the clinic due to deeper tissue penetration resulting from reduced absorption by cells/tissues and water, light scattering, and autofluorescence.

BODIPY (boron dipyrromethene difluoride, or 4,4-difluoro-4-bora-3a,4a-diaza-s-indacene) is a PS noted for high photostability, unique optical properties evidenced in sharp absorption and emission bands, high extinction coefficient, and high fluorescence quantum yields, as well as flexible synthesis and tunability. However, currently, among the BODIPY dyes used for PDT and in vivo imaging, none absorbs beyond 700 nm. Further, the synthesis of BODIPY derivatives has been complicated. It is to the development and use of NIR BODIPY dyes, and their production with greater ease and efficiency that the presently disclosed inventive concepts are presented.

In PDT a PS is administered and then the treatment site (e.g. tumor) is subjected to light irradiation to generate reactive oxygen species, especially singlet oxygen from oxygen, to damage target cells and tissues. When a PS is irradiated, it is converted to the triplet state via intersystem crossing from the singlet state. In what is known as the type II process, the triplet state PS transfers its energy to molecular oxygen to produce singlet oxygen. In a type I process, a chemical reaction of the excited PS with a substrate occurs, initiating an electron or proton transfer leading to the formation of radicals which react with molecular oxygen to produce reactive oxygen species such as superoxide, hydrogen peroxide, and hydroxyl ion.

BRIEF DESCRIPTION OF THE DRAWINGS

This patent or application file contains at least one drawing executed in color. Copies of this patent or patent application publication with color drawings will be provided by the Office upon request and payment of the necessary fee. The appended drawings illustrate several embodiments of the presently disclosed inventive concepts. It is to be noted however, that the appended drawings only illustrate several typical embodiments and are therefore not intended to be considered limiting of the scope of the presently disclosed inventive concepts.

DETAILED DESCRIPTION

Figure 1:
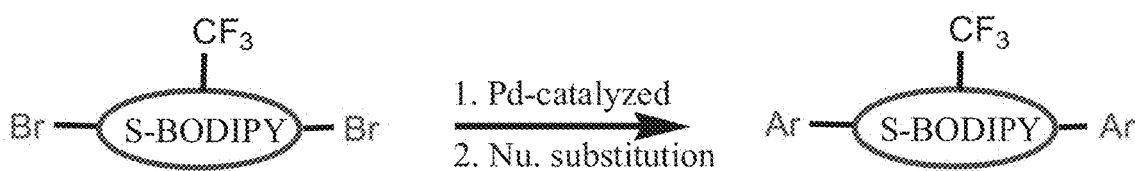
FIG. 1 is a schematic diagram of generalized synthetic strategy used in certain embodiments of the presently disclosed inventive concepts.

Before further describing various embodiments of the presently disclosed inventive concepts in more detail by way of exemplary description, examples, and results, it is to be understood that the presently disclosed inventive concepts are not limited in application to the details of methods and compositions as set forth in the following description. The presently disclosed inventive concepts are capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the presently disclosed inventive concepts may be practiced without these specific details. In other instances, features which are well known to persons of ordinary skill in the art have not been described in detail to avoid unnecessary complication of the description.

Unless otherwise defined herein, scientific and technical terms used in connection with the presently disclosed inventive concepts shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the presently disclosed inventive concepts pertain. All patents, published patent applications, and non-patent publications referenced in any portion of this application, including U.S. Provisional Application Ser. No. 61/912,251, filed on Dec. 5, 2013, are herein expressly incorporated by reference in their entirety to the same extent as if each individual patent or publication was specifically and individually indicated to be incorporated by reference.

All of the compositions and methods of production and application thereof disclosed herein can be made and executed without undue experimentation in light of the present disclosure. While the compositions and methods of the presently disclosed inventive concepts have been described in terms of particular embodiments, it will be apparent to those of skill in the art that variations may be applied to the compositions and/or methods and in the steps or in the sequence of steps of the method described herein without departing from the concept, spirit, and scope of the inventive concepts. All such similar substitutes and modifications apparent to those having ordinary skill in the art are deemed to be within the spirit, scope, and concept of the inventive concepts as defined herein.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal. Non-limiting examples of animals within the scope and meaning of this term include dogs, cats, rats, mice, guinea pigs, horses, goats, cattle, sheep, zoo animals, Old and New World monkeys, non-human primates, and humans.

"Treatment" refers to therapeutic treatments. "Prevention" refers to prophylactic or preventative treatment measures. The term "treating" refers to administering the composition to a patient for therapeutic purposes.

The terms "therapeutic composition" and "pharmaceutical composition" are used herein interchangeably and refer to an active agent-containing composition that may be administered to a subject by any method known in the art or otherwise contemplated herein, wherein administration of the composition brings about a therapeutic effect as described elsewhere herein. In addition, the compositions of the presently disclosed inventive concept may be designed to provide delayed, controlled, extended, and/or sustained release using formulation techniques which are well known in the art.

The term "effective amount" refers to an amount of an active agent which is sufficient to exhibit a detectable therapeutic effect without excessive adverse side effects (such as toxicity, irritation and allergic response) commensurate with a reasonable benefit/risk ratio when used in the manner of the inventive concepts. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

"Alkyl" means a saturated aliphatic branched or straight-chain monovalent hydrocarbon radical having the specified number of carbon atoms. For example, "($C_1$-$C_6$) alkyl" means a radical having from 1-6 carbon atoms in a linear or branched arrangement. "($C_1$-$C_6$) alkyl" includes but is not limited to methyl, ethyl, propyl, butyl, pentyl and hexyl.

"Alkenyl" means an unsaturated aliphatic branched or straight-chain divalent hydrocarbon radical having the specified number of carbon atoms. For example, "($C_1$-$C_6$) alkenyl" means a divalent unsaturated aliphatic radical having from 1-6 carbon atoms in a branched or linear arrangement and includes but is not limited to methylenyl, ethylenyl, propylenyl, butylenyl, pentylenyl and hexylenyl.

The term "alkoxy" means —O-alkyl; "hydroxyalkyl" means alkyl substituted with hydroxy; "aralkyl" means alkyl substituted with an aryl group; "heteroaralkyl" means alkyl substituted with a heteroaryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)-A*, wherein A* is alkyl; "alkoxycarbonyl" means —C(O)—OA*, wherein A* is alkyl; and where alkoxy is as defined above and includes but is not limited to methoxy, ethoxy, propoxy, butoxy, pentoxy and hexoxy.

The term "aryl" used alone or as part of a larger moiety as in "arylalkyl," "arylalkoxy," or "aryloxyalkyl," means carbocyclic aromatic rings. The term "carbocyclic aromatic group" may be used interchangeably with the terms "aryl," "aryl ring" "carbocyclic aromatic ring," "aryl group" and "carbocyclic aromatic group." An aryl group typically has 6-14 ring atoms. A "substituted aryl group" is substituted at any one or more substitutable ring atom. The term "aryl" as used herein also means a monocyclic, bicyclic or tricyclic carbocyclic ring system containing from 6 to 14 carbon atoms and includes phenyl, naphthyl, anthracenyl, 1,2-dihydronaphthyl, 1,2,3,4-tetrahydronaphthyl, fluorenyl, indanyl, indenyl and the like.

"Hetero" refers to the replacement of at least one carbon atom member in a ring system with at least one heteroatom selected from N, S, and O. A hetero ring system may have 1, 2, 3, or 4 carbon atom members replaced by a heteroatom depending on the size of the size of the ring system. 5- and 6-member rings may have 1 or 2 heteroatoms for example. The heteroatoms in the ring may be the same or different.

The term "heteroaryl," used alone or as part of a larger moiety as in "heteroarylalkyl" or "heteroarylalkoxy," refers to aromatic ring groups having five to fourteen ring atoms selected from carbon and at least one (typically 1-4, more typically 1 or 2) heteroatoms (e.g., oxygen, nitrogen or sulfur). They include monocyclic rings and polycyclic rings in which a monocyclic heteroaromatic ring is fused to one or more other carbocyclic aromatic or heteroaromatic rings. The term "heteroaryl" as used herein means a monocyclic, bicyclic or tricyclic ring system containing one or two aromatic rings and from 5 to 14 atoms of which, unless otherwise specified, one, two, three, four or five are heteroatoms independently selected from N, NH, N($C_{1-6}$ alkyl), O and S. The terms "haloalkyl" and "haloalkoxy" mean alkyl, alkoxy, as the case may be, substituted with one or more halogen atoms. "Halogen" and "halo" are interchangeably used herein and each refers to fluorine, chlorine, bromine, or iodine (F, Cl, Br, and I, respectively).

The following is a list of abbreviations which may be used herein: $^1O_2$: Singlet oxygen; $^1PS$: Singlet state photosensitizer; $^3O_2$: Molecular oxygen; $^3PS$: Triplet state photosensitizer, BODIPY: 4,4-difluoro-4-bora-3a,4a-diaza-s-indacene; BDP: BODIPY; $CDCl_3$: Deuterated chloroform; $CD_2Cl_2$: Deuterated methylene chloride; CMP: Core-modified porphyrin (dithiaporphyrin); DPBF: 1,3-diphenylisobenzofuran; DCM: Dichloromethane; DMSO-$d_6$: Deuterated dimethyl sulfoxide; DNA: Deoxyribonucleic acid; D-π-A: Donor-pi-acceptor; EtOH: Ethanol; HCl: Hydrochloric acid; HOMO: Highest occupied molecular orbital; HPLC: High pressure liquid chromatography; HPD: Haemotoporphyrin derivative; IP: Intraperitoneal; ISC: Inter-system crossing; ICG: Indocyanine green; LUMO: Lowest unoccupied molecular orbital; MeOH: Methanol; mTHPC: meta-tetrahydroxyphenylchlorin; mTHPBC: meta-tetrahydroxy-phenylbacteriochlorin; NMR: Nuclear magnetic resonance; NIR: Near infrared; PDD: Photodynamic diagnosis; PDT: Photodynamic therapy; PP: Phototoxic power, PS: Photosensitizer; PBS: Phosphate buffered saline solution; RT: Room temperature; SBDP: Sulfur BODIPY; TEA: Triethylamine; TFA: Trifluoroacetic acid; THF: Tetrahydrofuran; TLC: Thin layer chromatography; TTF: Tetrathiafulvalene; TCNQ: Tetracyano-p-quinodimethane; and UV: Ultra-Violet.

In certain embodiments, the presently disclosed inventive concepts are directed to novel synthetic methods which are versatile and robust for the production of various BODIPY derivatives (chromophores) which have absorbance in the near IR wavelengths. In certain embodiments, the presently disclosed inventive concepts include formation of stable intermediates for cross-coupling reactions and nucleophilic substitution to generate the NIR chromophores. In certain embodiments, these NIR chromophores have absorption in range including, but not limited to, from about 635 nm to about 850 nm. In certain embodiments the chromophores have a peak absorbance of at least 650 nm, or at least 660 nm, or at least 670 nm, or at least 680 nm, or at least 690 nm, or at least 700 nm, or at least 710 nm, or at least 720 nm, or at least 730 nm, or at least 740 nm, or at least 750 nm, or at least 760 nm, or at least 770 nm, or at least 780 nm, or at least 790 nm, or at least 800 nm, or at least 810 nm, or at least 820 nm, or at least 830 nm, or at least 840 nm, for example up to about 850 nm. These chromophores can be used in photodynamic therapy (PDT) as well as in vivo imaging. The dual functioning can be useful for example in the treatment via PDT of cancer in clinical practice. The presently disclosed inventive concepts therefore include, but are not limited to, novel NIR chromophores such as are described herein and compositions containing said chromophores, methods of their synthesis, and methods of their use in imaging and in photodynamic therapies such as the treatment of cancer. The chromophores can be used for conjugation to biomolecules and targeting vectors.

As noted above, the presently disclosed inventive concepts are directed to BODIPY derivatives (chromophores) which absorb in the Near IR ranges (e.g., 635 nm and greater), and to pharmaceutical compositions containing the derivatives, and to their methods of synthesis and use. In at least one embodiment, the presently disclosed inventive concepts include a compound represented by structural Formula (I) or pharmaceutically acceptable salts thereof:

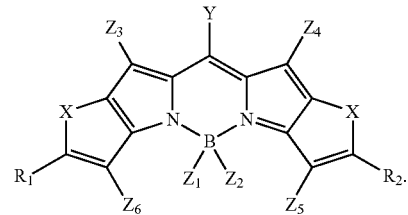

Formula (I)

In certain embodiments of Formula (I): (a) Y represents $CF_3$, $CCl_3$, $CBr_3$, $CI_3$, or $CH_3$; (b) X represents O, S, Se, or Te; (c) $Z_1$ and $Z_2$ are each independently selected from the group consisting of a halogen, alkyl, alkenyl, alkynyl, alkoxy, aryl, heteroaryl, heteroarylalkyl, and heteroarylalkoxy, wherein the heteroatom is O, S, or N; (d) $Z_3$, $Z_4$, $Z_5$, and $Z_6$ are each independently selected from the group consisting of hydrogen, a halogen, alkyl, alkenyl, alkynyl, alkoxy, aryl, heteroalkyl, heteroalkoxy, heteroaryl, heteroarylalkyl, heteroarylalkoxy, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N; and (e) $R_1$ and $R_2$ are each independently selected from the group consisting of a halogen, alkyl, alkenyl, alkynyl, alkoxy, aryl, haloaryl, haloheteroaryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein the $R_1$ and $R_2$ groups are substituted or non-substituted.

In at least one embodiment, the presently disclosed inventive concepts also include a compound represented by structural Formula (II) or a pharmaceutically acceptable salt thereof:

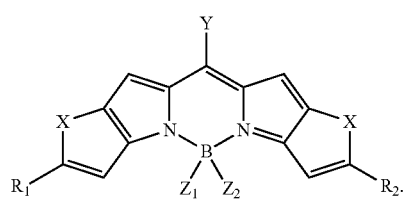

Formula (II)

In certain embodiments of Formula (II): (a) Y represents $CF_3$, $CCl_3$, $CBr_3$, $CI_3$, or $CH_3$; (b) X represents O, S, Se, or Te; (c) $Z_1$ and $Z_2$ each independently represents F, Cl, Br, or I; and (d) $R_1$ and $R_2$ are each independently selected from the group consisting of an alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein the $R_1$ and $R_2$ groups are substituted or non-substituted.

In at least one embodiment, the presently disclosed inventive concepts also include a compound represented by structural Formula (III) or a pharmaceutically acceptable salt thereof:

Formula (III)

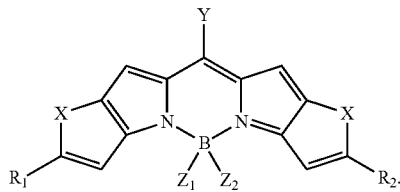

In certain embodiments of Formula (III): (a) Y represents $CF_3$, $CCl_3$, $CBr_3$, $CI_3$, or $CH_3$; (b) X represents O, S, Se, or Te; (c) $Z_1$ and $Z_2$ each independently represents F, Cl, Br, or I; and (d) $R_1$ and $R_2$ each independently represents F, Cl, Br, or I.

In at least one embodiment, the presently disclosed inventive concepts also include a compound represented by structural Formula (IV) or a pharmaceutically acceptable salt thereof:

Formula (IV)

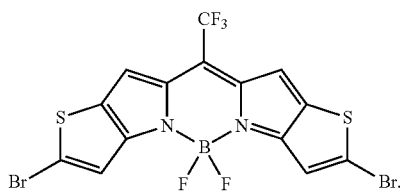

In at least one other embodiment of the compound represented by Formula (I), $Z_3$-$Z_6$ are hydrogen, and $R_1$ and $R_2$ are each independently selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein R1 and/or R2 are substituted or non-substituted.

In at least one other embodiment of the compound represented by Formula (I), at least two of $Z_3$-$Z_6$ comprise a halogen selected from the group consisting of Cl, F, Br, and I; and $R_1$ and $R_2$ are each independently selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein $R_1$ and/or $R_2$ are substituted or non-substituted.

In at least one other embodiment of the compound represented by Formula (I), wherein $R_1$ and $R_2$ and at least two of $Z_3$-$Z_6$ are each independently selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein $R_1$ and/or $R_2$ are substituted or non-substituted.

In the compounds noted above, in certain embodiments of the compounds of Formulas (I) and (II) above, $R_1$ and $R_2$ may each be independently selected from at least one of the following structures:

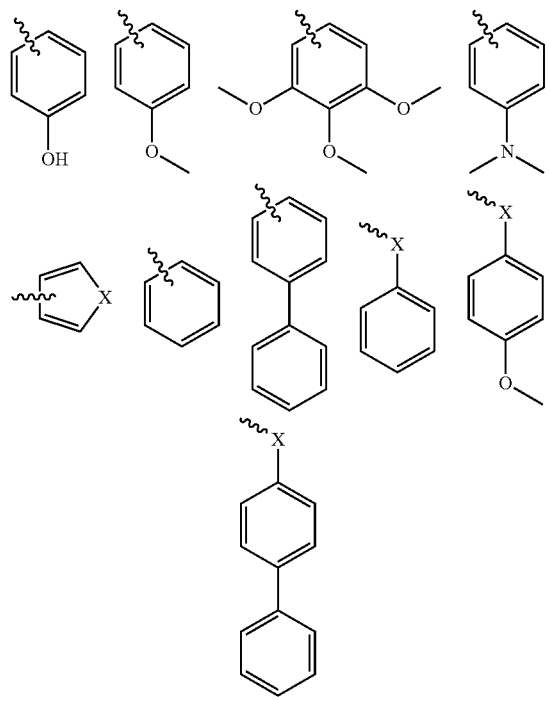

wherein X represents NH, O, or S.

As noted above, the presently disclosed inventive concepts are directed to methods of synthesis of BODIPY derivatives (chromophores) which absorb in the Near IR ranges. In at least one other embodiment, the presently disclosed inventive concepts include a method of synthesis. In the method, a compound represented by Formula (I) is utilized, wherein $Z_3$-$Z_6$ are hydrogen, and $R_1$ and $R_2$ are each independently selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein the modifying group is substituted or non-substituted. This compound is reacted with a halogenation agent under conditions which cause substitution of the hydrogen of at least two of $Z_3$-$Z_6$ with a halogen selected from the group consisting of Cl, F, Br, and I, thereby forming a halogenated compound wherein at least two of $Z_3$-$Z_6$ are each a halogen. For example, in certain embodiments, $R_1$ and $R_2$ may each be independently selected from, but are not limited to, at least one of the following structures:

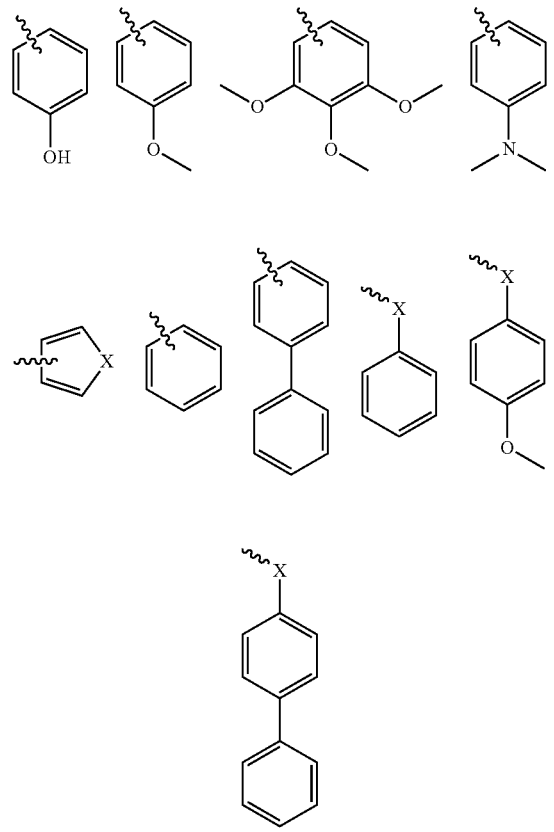

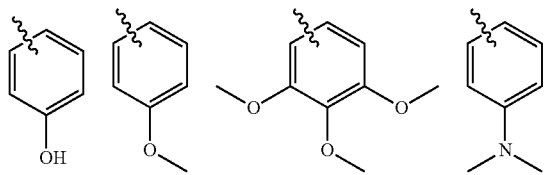

wherein X represents NH, O, or S.

In an additional synthesis method, the halogenated compound produced as described herein above (or an identical halogenated compound produced by any other method known in the art or otherwise contemplated herein) may be combined with a reactant able to provide a modifying group. In this method, the halogenated compound is reacted with the reactant under conditions suitable for causing substitution of each of the halogens of the at least two of $Z_3$-$Z_6$ with the modifying group from the reactant, thereby forming a derivative of said halogenated compound, wherein the modifying group is selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein the modifying group is substituted or non-substituted.

For example, the modifying group may be selected from, but is not limited to, at least one of the following structures:

wherein X represents NH, O, or S.

In at least one other embodiment, the presently disclosed inventive concepts include a method of synthesis in which the compound represented by Formula (III) or a pharmaceutical salt thereof is combined with a reactant able to provide a modifying group. The compound and reactant are reacted under conditions suitable for causing substitution of the $R_1$ and $R_2$ of said compound with the modifying group from the reactant, thereby forming a derivative of said compound, wherein the modifying group is selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein the modifying group is substituted or non-substituted. For example, the modifying group may be at least one of the following structures:

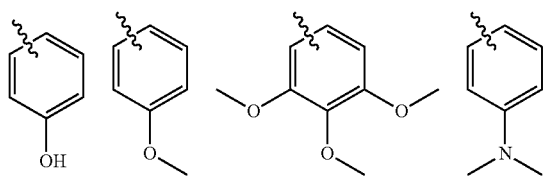

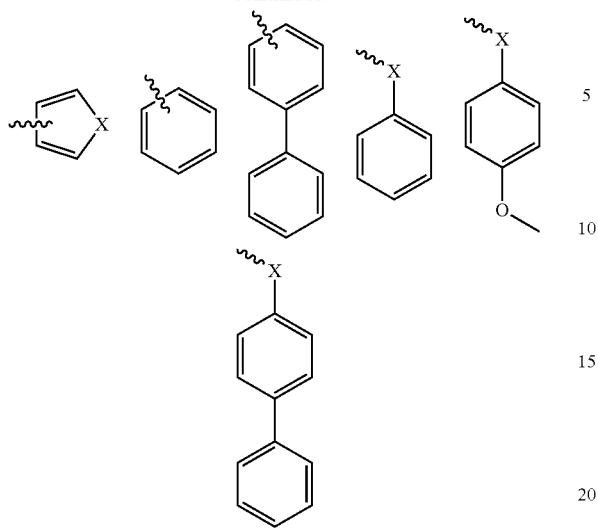

wherein X represents NH, O, or S.

In at least one other embodiment, the presently disclosed inventive concepts include a method of synthesis in which the compound represented by Formula (IV) or a pharmaceutical salt thereof is combined with a reactant able to provide a modifying group. The compound and reactant are reacted under conditions suitable for causing substitution of the two Br atoms of said compound with the modifying group from the reactant, thereby forming a derivative of said compound, wherein the modifying group is selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein the modifying group is substituted or non-substituted. For example, the modifying group may be at least one of the following structures:

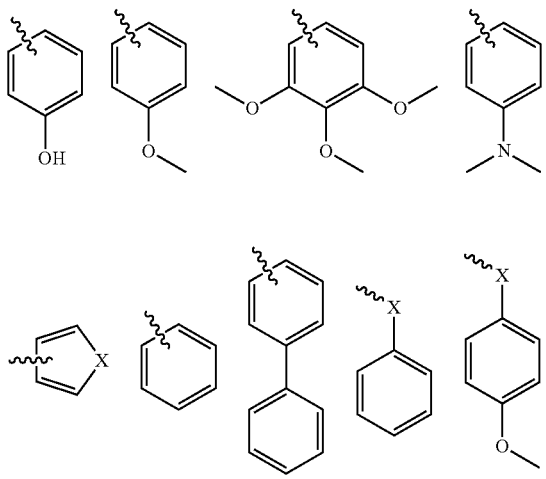

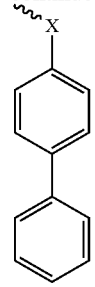

wherein X represents NH, O, or S.

EXAMPLES

The presently disclosed inventive concepts will be more readily understood by reference to the following examples and embodiments, which are included for purposes of illustration of certain aspects and embodiments of the presently disclosed inventive concepts, and are not intended to be limiting. The following detailed examples and methods describe how to make and use the various compounds of the presently disclosed inventive concepts and are to be construed, as noted above, only as illustrative, and not exhaustive of or limitations on the disclosure in any way whatsoever. Those skilled in the art will promptly recognize appropriate variations from the materials and procedures described herein.

Example 1

Synthesis of a Versatile NIR BODIPY Derivative Via Palladium-Catalyzed Cross-Coupling In at least one embodiment, the presently disclosed inventive concepts are directed to synthesis of the reactive fused BODIPY aryl halide compound 2,8-Di(bromo)-11-trifluoromethyl-dithieno[2,3-b]-[3,2-g]-5,5-difluoro-5-bora-3a,4a-dithio-s-indacene ("BDP635") displaying versatility with multiple Pd-catalyzed cross coupling reactions as well as nucleophilic substitution reactions (FIG. 1). This versatile compound is able to be further modified with various functional groups to modulate their physicochemical properties, such as but not limited to, water solubility and tendency of aggregation, as shown in examples and various embodiments below. In non-limiting embodiments of the presently disclosed inventive concepts, chemical reagents and solvents of analytical grade were purchased from commercial suppliers (Sigma-Aldrich Co., St. Louis, Mo.; or Acros Organics, Morris Plains, N.J.) and were used without purification. Air sensitive reactions were performed under an atmosphere of nitrogen. Nuclear magnetic resonance spectra were recorded in $CDCl_3$, $CD_2Cl_2$, or DMSO-$d_6$ Varian 300 MHz spectrometer. Chemical shifts are given in parts per million relative to $Me_4Si$ or $CHCl_3$ for $^1H$ NMR. Desorption Electron Impact (EI) and Electrospray Ionization (ESI) Mass Spectrometer measurements were recorded on Bruker Mass Spectrometer from SUNY Buffalo.

Figure 2:
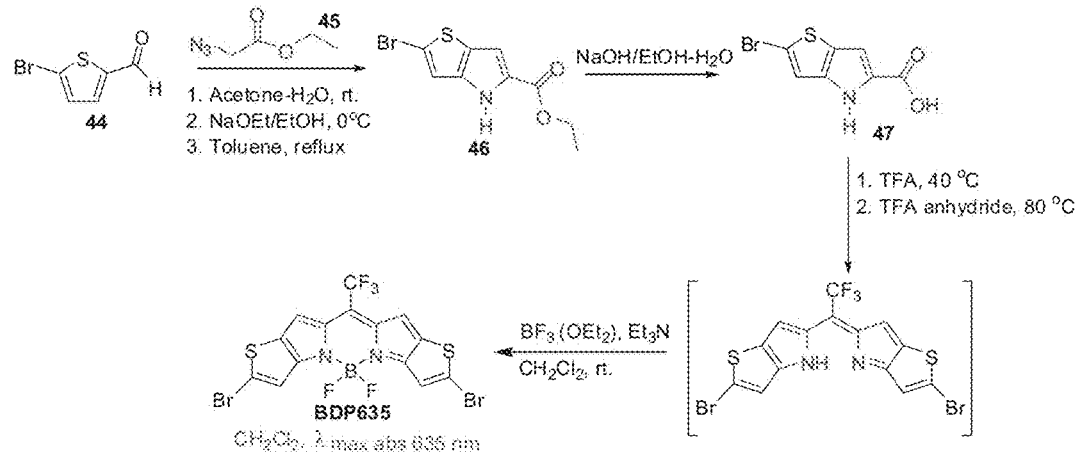
FIG. 2 is a scheme of the synthesis of the BDP635 compound.

Synthesis of the versatile BODIPY aryl halide BDP635: Synthesis of BDP635 is shown in FIG. 2. In one non-limiting embodiment, the pyrrole building block (compound 46) was formed by reacting 5-bromo-2-carbaldehyde (bromo-thiophene carbaldehyde) (compound 44) with ethylazidoacetate (compound 45) under heat, followed by basic hydrolysis. The carboxylic version of the modified pyrrole 2-bromo-4H-thieno[3,2-b]pyrrole-5-carboxylic acid (compound 47) was formed after acidification of 46. The bromo-substituted modified pyrrole (47) underwent a condensation via an acid catalyzed decarboxylation of the pyrrole and with a subsequent reaction with TFA anhydride installed a $CF_3$ at the meso-position of the formed dipyrromethene unit. The di-bromo BODIPY alkyl halide BDP635 was prepared by the reaction of the dipyrromethene unit with boron trifluoride ($BF_3$) and triethylamine. The BDY635 compound was isolated by silica-gel column chromatography by pouring the solution through the column to obtain a pure blue solution. The purified BDP635 was characterized by $^1$H-NMR and EI-HRMS.

Reaction conditions to obtain compound 47 (2-Bromo-4H-thieno[3,2-b]pyrrole-5-carboxylic acid): Compound 46 (0.30 g, 1.1 mmol) was dissolved in EtOH (10 ml). NaOH (0.62 g, 15.5 mmol) in water (4.9 ml) was added and refluxed for 1 hour. The reaction was cooled to room temperature and then chilled in an ice bath to acidify the mixture with concentrated HCl. The precipitate was filtered, washed with water, and dried under vacuum. A grey solid was obtained (0.22 mg, 70% [based on $^1$H-NMR]). $^1$H-NMR (DMSO-$d_6$, 300 MHz): δ 12.76 (s, 1H), 12.15 (s, 1H), 7.21 (s, 1H), 6.99 (s, 1H). HRMS ESI (m/z): Calculated for $C_7H_4BrNO_2S$: 246.0812. found: 246.0833 $[M+H]^+$.

Reaction conditions to obtain BDP635 (2,8-Di(bromo)-1-trifluoromethyl-dithieno[2,3-b]-[3,2-g]-5,5-difluoro-5-bora-3a,4a-dithio-s-indacene): Compound 47 (1.0 g, 1.8 mmol) was dissolved in TFA (25 ml) and heated to 40° C. for 15 minutes. An intense red color appeared. Trifluoroacetic anhydride (9 ml) was added, and the temperature was then raised to 80° C. with continued stirring for 4 hours. A deep blue color was observed. The reaction solution was allowed to cool and poured into an aqueous $NaHCO_3$ solution with crushed ice. The solution containing precipitates was then filtered, and the solid was dried in vacuo. The dry solid was dissolved in $CH_2Cl_2$ (250 ml) and stirred for 5 minutes at room temperature under a nitrogen atmosphere. Boron trifluoride dietherate (4 ml) and triethylamine (3 ml) were added, and the reaction was stirred at room temperature for 1 hour. The reaction solution was passed through a silica gel column using $CH_2Cl_2$ as eluent. An intense blue solution was obtained as pure compound which appeared as a bluish-green metallic solid (160 mg, 16% [based on $^1$H-NMR]). $^1$H-NMR (CDCl$_3$, 300 MHz): δ 7.31 (s, 2H), 7.24 (s, 2H). HRMS EI (m/z): Calculated for $C_{14}H_4BBr_2F_5N_2S_2$: 529.8200. Found: 529.8170$[M]^+$.

Figure 3:
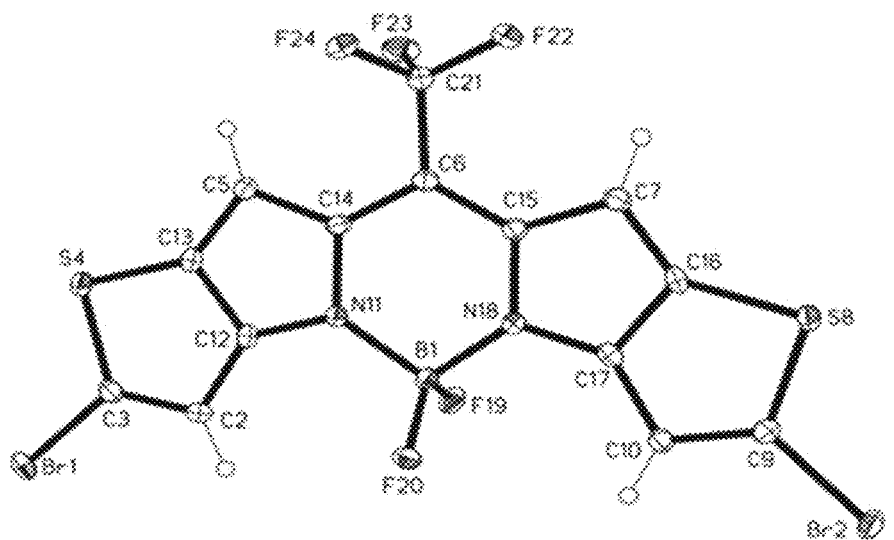
FIG. 3 depicts an ORTEP view of the X-ray crystal structure of BDP635. The displacement ellipsoids were drawn at the 50% probability level.

X-Ray Structure of BDP635: The structure of BDP635 was further confirmed by X-ray crystallography as a single pure structure. The BDP635 single crystal of a monoclinic system was obtained by slow evaporation from a clear blue, concentrated solution of BDP635 in $CH_2Cl_2$ at room temperature in a round bottom flask. The black plate-like crystal of dimensions 0.44×0.41×0.08 mm was used for the structural analysis. Measurements were performed using a diffractometer with a Bruker APEX CCD area detector and graphite-monochromated Mo Kα radiation (λ=0.71073 Å). The sterically crowded boron center maintained a geometry almost tetrahedral with an N—B—N angle of 105.1 (2)°, while the C—F—C and remained close to tetrahedral geometry at 106.7 (2)° and 106.3 (2)°. The Br—C bond lengths were identical at 1.861 (3) Å. The BODIPY core remained planar in fusion with the thiophene aromatic (see FIG. 3).

Figure 4:
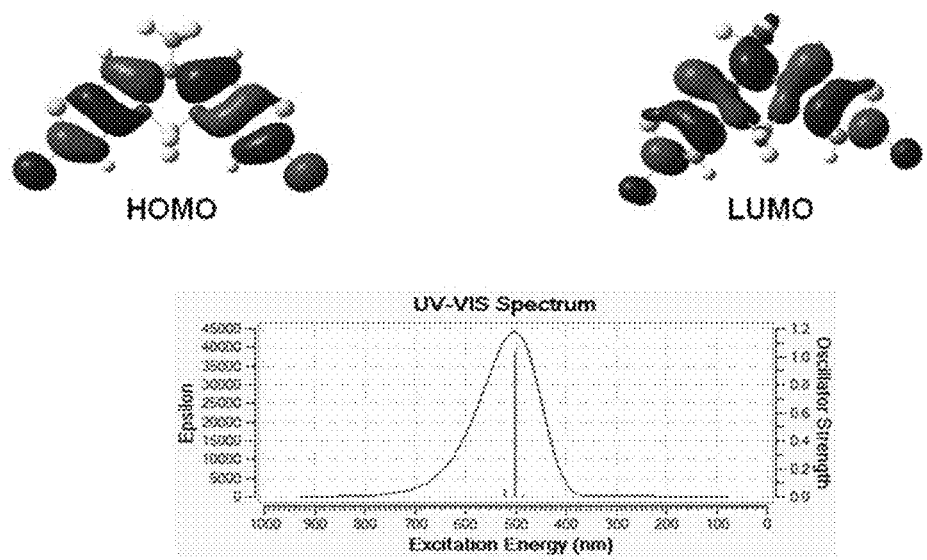
FIG. 4 depicts electron density maps of the frontier molecular orbitals of BDP635 and excited state UV prediction.

Quantum chemistry and theoretical approach: To gain insight into the electronic properties of BDP635, electron density maps of the frontier molecular orbitals (HOMO and LUMO) were calculated using density functional theory (DFT) calculations in tandem with the Becke's three-parameter hybrid functional and the Lee-Yang-Parr correlation (B3LYP). Gaussian 09 with an appropriate basis set of 6-311G* was used for the calculations. BDP635 showed similar electron density maps to previously synthesized NIR BODIPY dyes with the exception of donor fragments. In the ground state, the electrons at HOMO are held in the fused BODIPY chromophore, and once excited (LUMO), the electrons move to the trifluoromethyl electron withdrawing unit at the meso position (FIG. 4). The observed electron flow is expected in the design strategy for the donor-acceptor system. To gain insight into the excited states as a result of the strong absorption band in the visible region, a TDDFT excited state calculation at the B3LYP/6-311G* level in vacuo and the C-PCM model was performed, giving rise to a variation of ~135 nm between calculated vs. experimental (FIG. 4). Considering the strong $S_o \rightarrow S_1$ transitions with oscillator strength ~0.12, the variation could be attributed to solvent effects.

Examples 2-5

Formation of BDP635 Derivatives Via Palladium-Catalyzed Cross Coupling Reactions Carbon-carbon bond formation reactions are essential in chemical synthesis for a wide spectrum of uses mainly via cross coupling reactions. Transition metals have played an active role in promoting several cross-coupling reactions. Copper, palladium, nickel, and recently iron have been employed largely. Palladium is arguably the most used and thoroughly investigated.

To a large extent palladium uses iodides and bromides as its organic acceptors but recently alkyl phosphines, N-heterocyclic carbenes and aryl chlorides have become applicable. Each BDP635 derivative is referred to by the designation "SBDPiRxxx" where "xxx" refers to the approximate peak absorbance wavelength.

Example 2

Suzuki Cross Coupling

Figure 5:
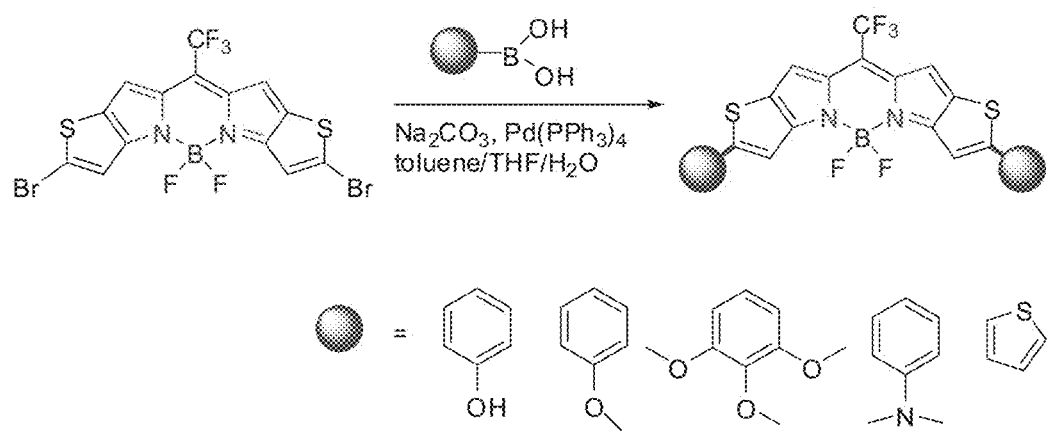
FIG. 5 depicts formation of derivatives of BDP635 based on a Suzuki reaction cross coupling.
Figure 6:
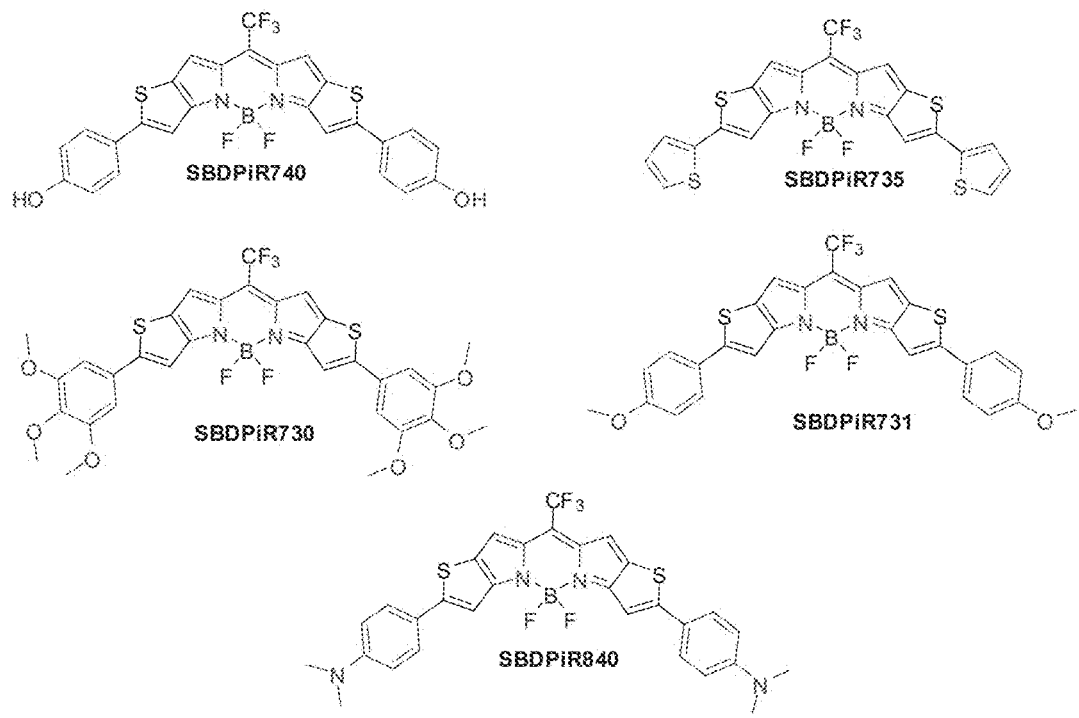
FIG. 6 depicts several non-limiting embodiments of BDY635 derivatives formed from the Suzuki reaction cross coupling.

FIG. 5 shows a Suzuki cross coupling reaction scheme for forming various derivatives of BDP635, for example based on aryl and thiophene R groups shown in the figure. Non-limiting embodiments of derivatives which can be formed in the reaction are shown in FIG. 6. Extension of the BDP635 compound pushes their absorption towards NIR. In the Suzuki cross coupling, BDP635 showed excellent reactivity in comparison to that of the hexabromo-BODIPY reported in the literature. In this Pd-catalyzed cross coupling reaction, the BDP635 reacted with different aryl boronic acids in a three component solvent system of water, THF and toluene, using Pd(PPh$_3$)$_4$ as catalyst with Na$_2$CO$_3$ as a base. The reaction was heated at 80° C. for 2-3 hours depending on arylboronic acid (FIG. 5). Compounds SBDPiR740, SBDPiR735, SBDPiR731, and SBDP730 (FIG. 6) were obtained using modifying group donor compounds 4-hydroxyphenylboronic acid, thiopheneboronic acid, methoxyphenylboronic acid, and 3,4,5-trimethoxyphenyl boronic acid, respectively, in moderate yields of ~50%. The use of modifying group donor compound N,N-dimethylaminophenylboronic acid resulted in SBDPiR840, the most red-shifted in the synthesized dye series. The enhanced resonance effect in the N,N-dimethylaminophenylboronic acid might have contributed to the relatively faster reaction in relation to the other substrates in the series.

Reaction conditions to obtain SBDPiR740 (2,8-Di(4-hydroxyphenyl)-11-trifluoromethyl-dithieno[2,3-b]-[3,2-g]-5,5-difluoro-5-bora-3a,4a-diaza-s-indacene): To a 1:1:1 toluene/THF/H$_2$O solution of BDP635 (0.19 g, 0.36 mmol) was added 4-hydroxyboronic acid (0.20 g, 1.43 mmol) and Na$_2$CO$_3$ (0.11 g 1.05 mmol). The reaction solution was purged by bubbling nitrogen gas through for 10 minutes. A catalytic amount of Pd(PPh$_3$)$_4$ (~5 mol %) was added, and the reaction was heated to 80° C. for 2 hours. After completion of the reaction as judged by TLC, the reaction was diluted with 5 ml water and extracted with diethyl ether. The combined organic layer was washed with water and brine and dried over anhydrous Na$_2$SO$_4$. The dried mixture was purified by silica-gel column chromatography using ethyl acetate-hexane (50:50) as eluent. A dark green solid was obtained (102 mg, 54%, [based on $^1$H-NMR]). $^1$H-NMR (acetone-d$_6$, 300 MHz): δ 7.84 (d, J=9.0 Hz, 4H), 7.52 (s, 2H), 7.37 (s, 2H) 7.03 (d, J=9.0 Hz, 4H). HRMS EI (m/z): Calculated for C$_{26}$H$_{14}$BF$_5$N$_2$O$_2$S$_2$: 556.0510. Found: 556.0520 [M]$^+$.

Reaction conditions to obtain SBDPiR731 (2,8-Di(4-methoxyphenyl)-11-trifluoromethyl-dithieno[2,3-b]-[3,2-g]-5,5-difluoro-5-bora-3a,4a-diaza-s-indacene): To a 1:1:1 toluene/THF/H$_2$O solution of BDP635 (0.10 g, 0.2 mmol) was added 4-methoxyphenylboronic acid (0.12 g, 0.8 mmol) and Na$_2$CO$_3$ (0.06 g 0.6 mmol). The reaction solution was purged by bubbling nitrogen gas through for 10 minutes. A catalytic amount of Pd(PPh$_3$)$_4$ (~5 mol %) was added, and the reaction was heated to 80° C. for 2 hours. After completion of the reaction as judged by TLC, the reaction was diluted with 5 ml water and extracted with diethyl ether. The combined organic layer was washed with water and brine and dried over anhydrous Na$_2$SO$_4$. The dried mixture was purified by silica-gel column chromatography using ethyl acetate-toluene (5:95) as eluent. A dark green solid was obtained (53 mg, 50% [based on $^1$H-NMR]). $^1$H-NMR (CD$_2$Cl$_2$, 400 MHz): δ 7.76 (d, J=8.0 Hz, 4H), 7.34 (s, 2H), 7.32 (s, 2H), 7.03 (d, J=8.0 Hz, 4H), 3.91 (s, 6H). HRMS EI (m/z): Calculated for C$_{28}$H$_{18}$BF$_5$N$_2$O$_2$S$_2$: 584.0823. Found: 584.0825 [M]$^+$.

Reaction conditions to obtain SBDPiR735 (2,8-Di(thiophenyl)-11-trifluoromethyl-dithieno[2,3-b]-[3,2-g]-5,5-difluoro-5-bora-3a,4a-diaza-s-indacene): To a 1:1:1 toluene/THF/H$_2$O solution of BDP635 (0.10 g, 0.2 mmol) was added 2-thiopheneboronic acid (0.10 g, 0.8 mmol) and Na$_2$CO$_3$ (0.06 g 0.6 mmol). The reaction solution was purged by bubbling nitrogen gas through for 10 minutes. A catalytic amount of Pd(PPh$_3$)$_4$ (~5 mol %) was added, and the reaction was heated to 80° C. for 30 minutes. After completion of the reaction as judged by TLC, the reaction was diluted with 5 ml water and extracted with diethyl ether. The combined organic layer was washed with water and brine and dried over anhydrous Na$_2$SO$_4$. The dried mixture was purified by silica-gel column chromatography using ethyl acetate-toluene (5:95) as eluent. A dark green solid was obtained (51 mg, 50% [based on $^1$H-NMR]). $^1$H-NMR (CD$_2$Cl$_2$, 300 MHz): δ 7.24 (m, 2H), 7.53 (s, 2H), 7.54 (s, 2H), 7.34 (s, 2H), 7.57 (m, 4H). HRMS EI (m/z): Calculated for C$_{22}$H$_{10}$BF$_5$N$_2$S$_4$: 535.9740. Found: 535.9725 [M]$^+$.

Reaction conditions to obtain SBDPiR730 (2,8-Di(3,4,5-trimethoxyphenyl)-11-trifluoromethyl-dithieno[2,3-b]-[3,2-g]-5,5-difluoro-5-bora-3a,4a-diaza-s-indacene): To a 1:1:1 toluene/THF/H$_2$O solution of BDP635 (0.12 g, 0.2 mmol) was added 3,4,5-trimethoxyphenylboronic acid (0.19 g, 0.9 mmol) and Na$_2$CO$_3$ (0.07 g, 0.7 mmol). The reaction solution was purged by bubbling nitrogen gas through for 10 minutes. A catalytic amount of Pd(PPh$_3$)$_4$ (~10 mol %) was added and the reaction heated to 80° C. for 1 hour. After completion of the reaction as judged by TLC, the reaction solution was diluted with 10 ml toluene, and the water layer was separated. The organic layer was washed with water and brine and dried over anhydrous Na$_2$SO$_4$. The dried mixture was purified by silica-gel column chromatography using ethyl acetate-toluene (5:95) as eluent. A dark green solid was obtained (54 mg, 45% [based on $^1$H-NMR]). $^1$H-NMR (CD$_2$Cl$_2$, 300 MHz): δ 7.36 (s, 2H), 7.32 (s, 2H), 6.98 (s, 4H), 3.93 (s, 12H), 3.87 (s, 6H). HRMS EI (m/z): Calculated for C$_{32}$H$_{26}$BF$_5$N$_2$O$_6$S$_2$: 704.1245. Found: 704.1226 [M]$^+$.

Reaction conditions to obtain SBDPiR840 (2,8-Di(4-N,N,dimethylaminophenyl)-11-trifluoromethyl-dithieno[2,3-b]-[3,2-g]-5,5-difluoro-5-bora-3a,4a-diaza-s-indacene): To a 1:1:1 toluene/THF/H$_2$O solution of BDP635 (0.12 g, 0.2 mmol) was added 4-N,N,dimethylaminophenylboronic acid (0.11 g, 0.7 mmol) and Na$_2$CO$_3$ (0.07 g 0.7 mmol). The reaction solution was purged by bubbling nitrogen gas through for 10 minutes. A catalytic amount of Pd(PPh$_3$)$_4$ (~10 mol %) was added, and the reaction was heated to 80° C. for 2 hours. After completion of the reaction as judged by TLC, the reaction was diluted with 10 ml toluene and the water layer separated. The organic layer was washed with water and brine and dried over anhydrous Na$_2$SO$_4$. The dried mixture was purified by silica-gel column chromatography using toluene as eluent. A dark green solid was obtained (24 mg, 20% [based on $^1$H-NMR]). $^1$H-NMR (CD$_2$Cl$_2$, 300 MHz): δ 7.68 (d, J=6.0 Hz, 4H), 7.37 (s, 2H), 7.34 (s, 2H), 7.40 (d, J=6.0 Hz, 4H), 3.07 (s, 9H), HRMS EI (m/z): Calculated for C$_{30}$H$_{24}$BF$_5$N$_4$S$_2$: 610.1456. Found: 610.1470 [M]$^+$.

Example 3

Heck Reaction

Figure 7:
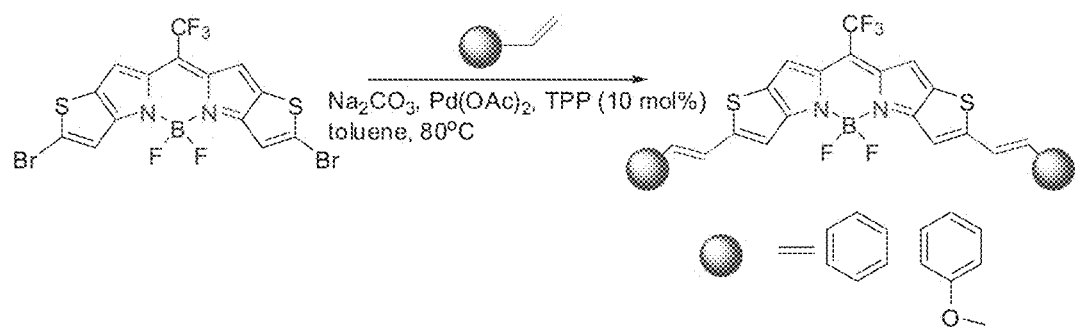
FIG. 7 depicts formation of derivatives of BDP635 based on a Heck reaction coupling.
Figure 8:
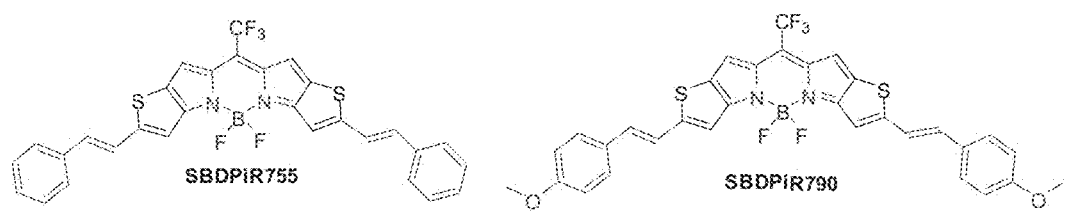
FIG. 8 depicts several non-limiting embodiments of BDY635 derivatives formed from the Heck reaction coupling.

In the D-π-A system, an approach to extend the π-conjugated system sandwiched by the donor and acceptor systems was performed. Hence the Heck reaction (FIGS. 7-8) provided a useful tool for building substituted olefins derivatives of BDP635. In an anhydrous toluene solution of BDP635 with respective styrene and 4-methoxystyrene substrates were heated to 80° C. for 6 hours. Palladium (II) acetate (10 mol %) was used as catalyst and triphenylphosphine (10 mol %) as ligand. Shorter reaction times yielded the monosubstituted analogues as observed on TLC and UV-vis spectroscopy but were not isolated and characterized. The commonly used base for Heck coupling, triethylamine, was not employed for these substrates; instead. Na$_2$CO$_3$ was used. SBDPiR755 and SBDPiR790 (FIG. 8) were obtained in acceptable yields of 25-30%. A remarkable bathochromic shift was observed due to the external olefin added to the existing BODIPY π-system to afford a D-π-π-A system. The H-NMR and HRMS confirmed SBDPiR755 and SBDPiR790, as generated compounds in yields of 35%.

Reaction conditions to obtain SBDPiR755 (2,8-Di (styryl)-11-trifluoromethyl-dithieno[2,3-b]-[3,2-g]-5,5-difluoro-5-bora-3a,4a-diaza-s-indacene): In a one-neck flask BDP635 (0.08 g, 0.2 mmol), styrene (0.04 g, 0.4 mmol), Pd(OAc)$_2$ (20 mol %), triphenylphosphine (20 mol %), and Na$_2$CO$_3$ (0.06 g 0.6 mmol) were dissolved in anhydrous toluene (3 ml). The reaction solution was heated to 80° C. with stirring under N$_2$ (g) for 6 hours. After completion (monitored by TLC), the reaction was diluted with 10 ml toluene, washed with water and brine, and dried over anhydrous $Na_2SO_4$. The dried mixture was purified by silica-gel column chromatography using toluene as eluent. A black solid was obtained (17 mg, 22% [based on $^1$H-NMR]). $^1$H-NMR ($CD_2Cl_2$, 300 MHz): δ 7.59 (d, J=8.0 Hz, 4H), 7.39 (d, J=8.0 Hz, 4H), 7.26 (s, 3H), 7.20 (s, 1H), 7.12 (s, 2H). HRMS EI (m/z): Calculated for $C_{30}H_{18}BF_5N_2S_2$: 576.0925. Found: 576.0906 $[M]^+$.

Reaction conditions to obtain SBDPiR790 (2,8-Di(4-(methoxy-phenyl)vinyl)-11-trifluoromethyl-dithieno[2,3-b]-[3,2-g]-5,5-difluoro-5-bora-3a,4a-diaza-s-indacene): In a one-neck flask BDP635 (0.08 g, 0.2 mmol), 4-methoxystyrene (0.04 g, 0.4 mmol), $Pd(OAc)_2$ (20 mol %), triphenylphosphine (20 mol %), and $Na_2CO_3$ (0.06 g 0.6 mmol) were dissolved in anhydrous toluene (3 ml). The reaction solution was heated to 80° C. with stirring under $N_2$ (g) for 6 hours. After completion (monitored by TLC), the reaction was diluted with 10 ml toluene, washed with water and brine, and dried over anhydrous $Na_2SO_4$. The dried mixture was purified by silica-gel column chromatography using toluene as eluent. A dark brown solid was obtained (20 mg, 25% [based on $^1$H-NMR]). $^1$H-NMR ($CD_2Cl_2$, 300 MHz): δ 7.44 (d, J=9.0 Hz, 4H), 7.17 (s, 2H), 7.16 (s, 2H), 7.15 (s, 2H), 6.99 (s, 2H), 6.88 (d, J=9.0 Hz, 4H). HRMS EI (m/z): Calculated for $C_{12}H_{22}BF_5N_2O_2S_2$: 636.1136. Found: 636.1120 $[M]^+$.

Example 4

Stille Coupling

Figure 9:
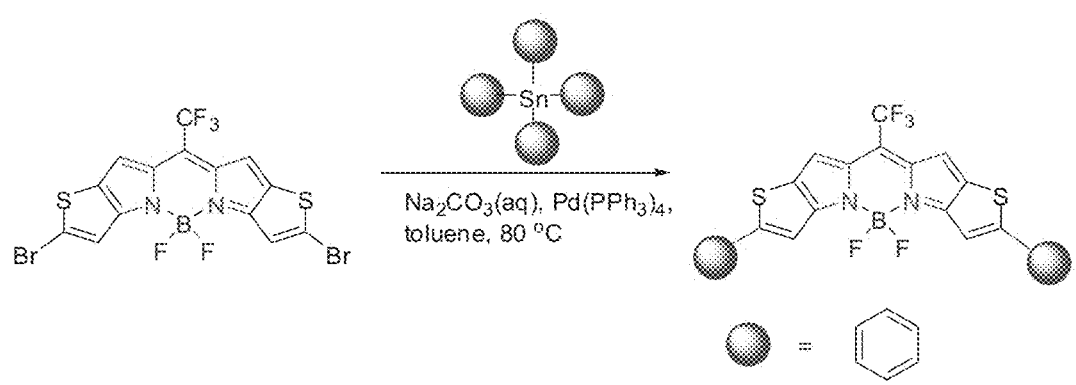
FIG. 9 depicts formation of derivatives of BDP635 based on a Stille cross-coupling reaction.
Figure 10:
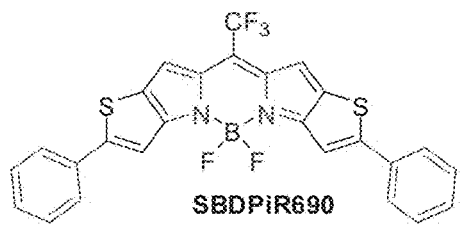
FIG. 10 depicts several non-limiting embodiments of BDP635 derivatives formed from the Stille reaction cross coupling.

An alternative to the organoborane reagent is the organostannanes (organotin) as typified in the Stille cross coupling shown in FIGS. 9-10. It was considered that building an organic electrophile would be an excellent coupling partner for organostannanes, in addition to the wide functional group tolerance, less sensitivity to moisture, and relatively easier preparation. BDP635 was allowed to react under the Stille coupling reaction conditions and heated to 80° C. for 1 hour with equimolar portions of tetraphenyl tin reagent. Tetrakis(triphenylphosphine)palladium ($Pd(PPh_3)_4$) was used as catalyst with an aqueous solution of $Na_2CO_3$ (1M) to afford the SBDPiR690 (FIG. 10) in a di-substituted fashion. The reaction mixture was cooled, washed with water and brine, and dried over anhydrous $Na_2SO_4$. Purification by silica gel column chromatography using 100% Toluene-95% Toluene-EA yielded SBDPiR690 in moderate yields of ~50%.

Reaction conditions to obtain SBDPiR690 (2,8-Di(phenyl)-1-trifluoromethyl-dithieno[2,3-b]-[3,2-g]-5,5-difluoro-5-bora-3a,4a-diaza-s-indacene): In a one-neck flask, BDP635 (0.03 g, 0.1 mmol), tetraphenyltin (0.03 g, 0.1 mmol), $Pd(OAc)_2$ (20 mol %), triphenylphosphine (20 mol %), and $Na_2CO_3$ (2 ml, 1 M aq.) were dissolved in toluene (3 ml). The reaction solution was heated to 80° C. with stirring under $N_2$ (g) for 1 hour. After completion (monitored by TLC), the reaction was diluted with 10 ml toluene, washed with water and brine, and dried over anhydrous $Na_2SO_4$. The dried mixture was purified by silica-gel column chromatography using toluene as eluent. A green solid was obtained (10 mg, 30% [based on $^1$H-NMR]). $^1$H-NMR ($CD_2Cl_2$, 300 MHz): δ 7.52 (d, J=8.0 Hz, 4H), 7.40 (s, 2H), 7.31 (peaks overlap, 6H), 7.24 (s, 2H). HRMS EI (m/z): Calculated for $C_{26}H_{14}BF_5N_2S_2$: 524.0612. Found: 524.0599 $[M]^+$.

Example 5

Nucleophilic Substitution

Figure 11:
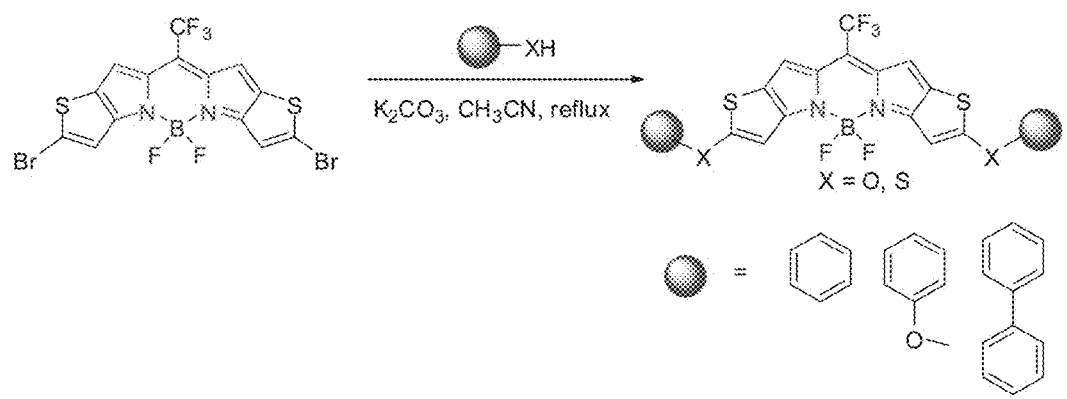
FIG. 11 depicts formation of derivatives of BDP635 based on a nucleophilic substitution reaction.
Figure 12:
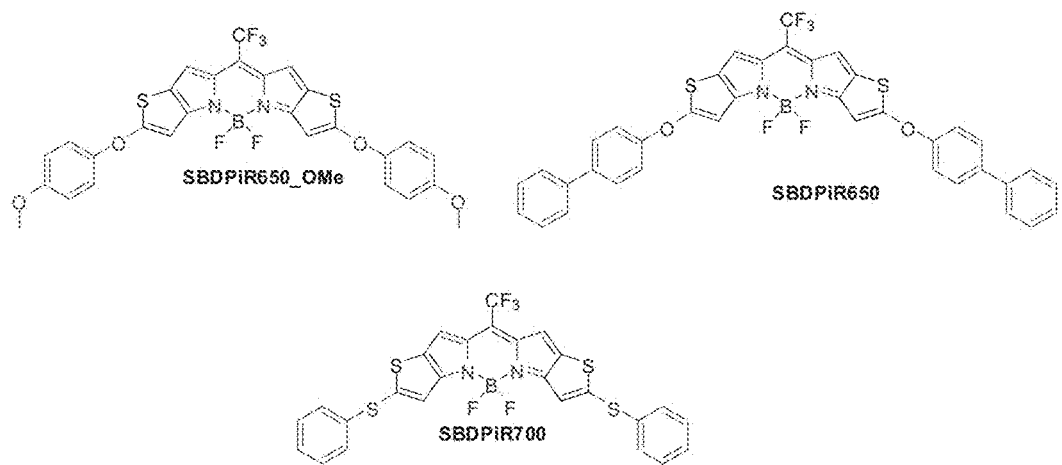
FIG. 12 depicts several non-limiting embodiments of BDP635 derivatives formed from the nucleophilic substitution reaction.

Substitution reactions with nucleophiles from the chalcogen group; O and S were performed as depicted in FIGS. 11 and 12. Relatively fast reactions were observed with appreciably moderate to high yields, confirming the versatility of BDP635 as a base compound. $S_NAr$ reactions on BDP635 with varied nucleophiles such as thiophenol, 4-methoxyphenol, and biphenylphenol produced SBDPiR700, SBDPiR650_OMe, and SBDPiR650, respectively (FIG. 12). The reaction conditions for the substrates utilized minimal amount of acetonitrile and $K_2CO_3$ as base to establish the $S_NAr$. BDP635, arylnucleophile (thiophenol or substituted phenols), and $K_2CO_3$ were dissolved in a minimal amount of acetonitrile, and the reaction was refluxed at 80° C. for 30 minutes. The reaction mixture was cooled, and the solvent was removed. The residue was dissolved in $CH_2Cl_2$ and washed with water and brine. Purification by silica gel column using 80% Hexane-EA afforded SBDPiR700, SBDPiR650 and SBDPiR650_OMe in high yields (~60-70%).

Reaction conditions to obtain SBDPiR700 (2,8-Di(thiophenoxy)-11-trifluoromethyl-dithieno[2,3-b]-[3,2-g]-5,5-difluoro-5-bora-3a,4a-diaza-s-indacene): BDP635 (0.03 g, 0.06 mmol), thiophenol (0.02 g, 0.14 mmol), and $K_2CO_3$ (0.02 g, 0.14 mmol) were dissolved in anhydrous $CH_3CN$ (3 ml). The reaction solution was heated to 80° C. with stirring under $N_2$ (g) for 30 minutes; the reaction turned brick red. After completion (monitored by TLC), the reaction was diluted with 10 ml ether, washed with 1 M $Na_2CO_3$ (aq.), and dried over anhydrous $Na_2SO_4$. The dried mixture was purified by silica-gel column chromatography using toluene as eluent. A green solid was obtained (10 mg, 30% [based on $^1$H-NMR]). $^1$H-NMR ($CD_2Cl_2$, 300 MHz): δ 7.62 (d, J=6.0 Hz, 4H), 7.47 (d, J=6.0 Hz, 4H), 7.24 (s, 2H), 7.15 (s, 2H), 6.91 (s, 2H). HRMS EI (m/z): Calculated for $C_{26}H_{14}BF_5N_2S_4$: 588.0053. Found: 588.0037 $[M]^+$.

Reaction conditions to obtain SBDPiR650_OMe (2,8-Di(4-methoxyphenoxy)-11-trifluoromethyl-dithieno[2,3-b]-[3,2-g]-5,5-difluoro-5-bora-3a,4a-diaza-s-indacene): BDP635 (0.06 g, 0.1 mmol), 4-methoxyphenol (0.06 g, 0.3 mmol), and $K_2CO_3$ (0.05 g, 0.4 mmol) were dissolved in anhydrous $CH_3CN$ (3 ml). The reaction solution was heated to 80° C. with stirring under $N_2$ (g) for 30 minutes. After completion (monitored by TLC), the reaction was dried, dissolved in $CH_2Cl_2$, washed with water and brine, and dried over anhydrous $Na_2SO_4$. The dried mixture was purified by silica-gel column chromatography using hexane as eluent. A blue solid was obtained (15 mg, 25%, [based on $^1$H-NMR]). $^1$H-NMR ($CD_2Cl_2$, 300 MHz): δ 7.09 (d, J=8.0 Hz, 4H) 7.00 (s, 2H), 6.85 (d, J=8.0 Hz, 4H), 6.21 (s, 2H), 3.77 (s, 6H). HRMS EI (m/z): Calculated for $C_{28}H_{18}BF_5N_2O_4S_2$: 616.0721. Found: 616.0724 $[M]^+$.

Reaction conditions to obtain SBDPiR650 (2,8-Di(biphenyl-4-yloxy)-11-trifluoromethyl-dithieno[2,3-b]-[3,2-g]-5,5-difluoro-5-bora-3a,4a-diaza-s-indacene): BDP635 (0.06 g, 0.1 mmol), 4-phenylphenol (0.06 g, 0.3 mmol), and $K_2CO_3$ (0.05 g, 0.4 mmol) were dissolved in anhydrous $CH_3CN$ (3 ml). The reaction solution was heated to 80° C. with stirring under $N_2$ (g) for 30 minutes. After completion (monitored by TLC), the reaction was diluted with 10 ml toluene, washed with water and brine, and dried over anhydrous $Na_2SO_4$. The dried mixture was purified by silica-gel column chromatography using ethyl acetate-hexane (50:50) as eluent. A reddish-brown solid was obtained (42 mg, 70% [based on $^1$H-NMR]). $^1$H-NMR ($CDCl_3$, 300 MHz): δ 7.52 (m, 3H), 7.49 (m, 5H) 7.43 (m, 5H), 7.30 (d, J=9.0 Hz, 3H), 7.20 (s, 1H), 6.80 (d, J=9.0 Hz, 2H), 6.39 (s, 1H). HRMS EI (m/z): Calculated for $C_{38}H_{22}BF_5N_2O_2S_2$: 708.1136. Found: 708.1121 [M]$^+$.

All substrates were purified by silica gel column chromatography and characterized by $^1$H-NMR and EI-HRMS. All synthesized analogs were new compounds except SBDPiR731 (39), which was synthesized previously. The reaction conditions and yields of the palladium-catalyzed coupling reactions as well as $S_NAr$ reactions of BDP635 are summarized below in Table 1.

TABLE 1

Summary of Reaction Conditions of Palladium Catalyzed and Nucleophilic Substitution of SBDPiRs

| Reagent | Solvent | Temp/ °C. | Reaction time/h | Product | Yield/ % |
|---|---|---|---|---|---|
| 4-Methoxyphenol | CH$_3$CN | reflux | 1 | SBDPiR650_OMe | 25 |
| 4-Phenylphenol | CH$_3$CN | reflux | 1 | SBDPiR650 | 70 |
| Thiophenol | CH$_3$CN | reflux | 0.5 | SBDPiR700 | 30 |
| Tetraphenyltin | Toluene | 80 | 1 | SBDPiR690 | 30 |
| Styrene | Toluene | 80 | 6 | SBDPiR755 | 20 |
| 4-Methoxystyrene | Toluene | 80 | 6 | SBDPiR790 | 25 |
| 4-Hydroxyboronic acid | Tol/THF/H$_2$O$^a$ | 80 | 3 | SBDPiR740 | 54 |
| 4-methoxyphenyl boronic acid | Tol/THF/H$_2$O$^a$ | 80 | 3 | SBDPiR731 | 50 |
| 3,4,5-trimethoxy phenylboronic acid | Tol/THF/H$_2$O$^a$ | 80 | 2 | SBDPiR730 | 45 |
| N,N-dimethylphenyl boronic acid | Tol/THF/H$_2$O$^a$ | 80 | 2 | SBDPiR840 | 20 |
| 2-thiopheneboronic acid | Tol/THF/H$_2$O$^a$ | 80 | 1 | SBDPiR735 | 50 |

Tol—toluene;
$^a$1:1:1 (v/v)

Optical Properties of the BDP635 Derivatives

Absorption: The BDP635 derivatives showed excellent photophysical properties with high extinction coefficients, sharp absorption, and emission bands similar to the cyanines and phthalocyanines. The high extinction coefficient could be attributed to the planarity of these SBDPiRs, as shown by the X-ray single crystal analysis of the precursor BDP635. The optical characteristics validated the rational approach used in the design. The previous D-π-A strategy was adopted, displaying absorption spectra with lowest energy absorbing maximally 650-840 nm, which corresponds to the 0-0 band of $S_o \rightarrow St$ (π-π*) transition of the BODIPY framework. The nucleophilic substituted SBDPiRs exhibited lowest absorption maxima among the series due to the break in conjugation as a result of the heteroatom (O, S) insertion. The impact of the sulfur heavy atom in SBDPiR700 gave a pronounced bathochromic shift relative its oxygen analogues. In contrast, the Suzuki and Stille reactions made SBDPiRs as a result of uninterrupted conjugation to aromatics (SBDPiR690), heteroaromatics (SBDPiR735), and aromatics bearing modifying groups such as the 4-methoxyphenyl, 4-hydroxyphenyl, and 3,4,5-trimethoxyphenyl (SBDPiR730, SBDPiR731, SBDPiR740) displayed enhanced red-shift towards NIR absorption. Interestingly, SBDPiR840 having a 4-N,N-dimethylaminophenyl group as a modifying group showed a large $S_o \rightarrow S_1$ transition, with the lowest energy, presumably, as a result of the intramolecular charge transfer (ICT) imposed by the dimethylaminophenyl substituent, which significantly reduced the HOMO-LUMO gap.

Figure 13:
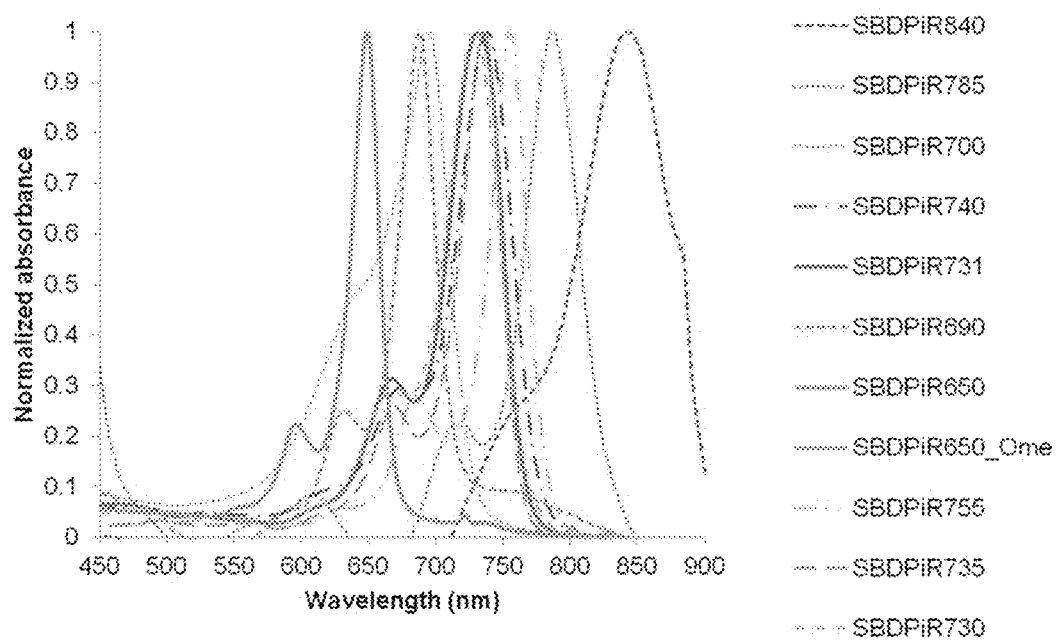
FIG. 13 shows absorption and emission spectra of BDP635 derivatives.
Figure 14:
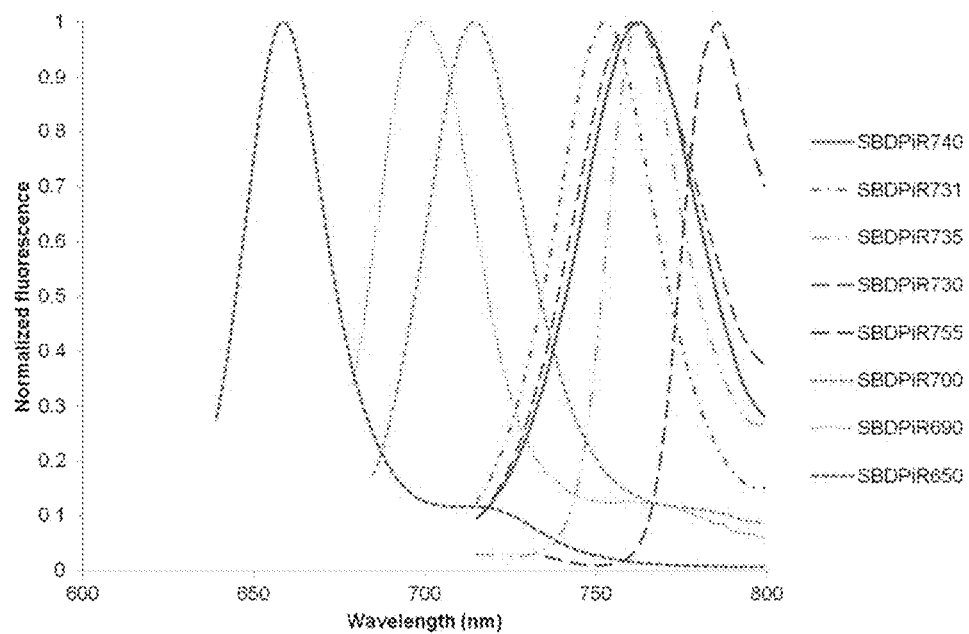
FIG. 14 shows absorption and emission spectra of BDP635 derivatives.

The fluorescence spectra of these SBDPiRs showed emission in the NIR from 660 nm to >800 nm, making them similar or better than cyanine dye series which are widely used. The sharp emission bands and almost no spectral overlap with its absorption band as observed (FIGS. 13-14 and Table 2) render these SBDPiRs akin to available quantum dots. In addition, spectral separations render these SBDPiRs useful for cellular and in vivo imaging as well as multicolor assays.

TABLE 2

Optical Properties of BDP635 and Derivative SBDPiRs

| Dye | $\lambda_{abs}$, nm | $\lambda_{flu}$, nm | $\epsilon$, M$^{-1}$ cm$^{-1}$ |
|---|---|---|---|
| BDP635 | 635 | 650 | — |
| SBDPiR650_OMe | 649 | 660 | 118 000 |

TABLE 2-continued

Optical Properties of BDP635 and Derivative SBDPiRs

| Dye | $\lambda_{abs}$, nm | $\lambda_{flu}$, nm | $\epsilon$, M$^{-1}$ cm$^{-1}$ |
|---|---|---|---|
| SBDPiR650 | 649 | 660 | 83 000 |
| SBDPiR690 | 688 | 700 | 120 000 |
| SBDPiR700 | 694 | 715 | 105 000 |
| SBDPiR730 | 728 | 761 | 140 000 |
| SBDPiR731 | 731 | 755 | 185 000 |
| SBDPiR735 | 733 | 763 | 125 000 |
| SBDPiR740 | 738 | 763 | 101 000 |
| SBDPiR755 | 753 | 785 | 110 000 |
| SBDPiR790 | 786 | — | 85 000 |
| SBDPiR840 | 841 | — | — |

Example 6

In Vivo Imaging with SBDPiR790

Materials and Methods

Female Balb/c mice were purchased from NCI (Federick, Md.). Mice were housed and handled in the College of Pharmacy animal facility, University of Oklahoma Health Sciences Center, Oklahoma City, Okla. All animal experiments were approved by IACUC, University of Oklahoma Health Sciences Center (personal approval was offered). Injection solution of SBDPiR790 was prepared by solubilizing it in DMSO (4 mM), and then it was diluted with 1% Tween 80-5% dextrose solution (PBS). The solution was filtered through a 0.2 µm sterile syringe filter before i.p. injection.

BALB/c mice bearing colon-26 cells (mouse colon carcinoma cells) were used for this study. 6-8 week old Balb/c mice were shaved and depilated with hair removal cream (Nair) at the upper back. The mice were subcutaneously inoculated with colon 26 cells at the neck region with 1×10⁻⁶ cells in 0.1 ml PBS solution. Tumors with 4-6 mm diameter size were made in a week. The in vivo Xtreme imaging system (Carestream Health, Inc.) was used in acquiring images as mice were kept under safe anaesthesia using Isoflurane. The instrumental conditions for the imaging were as follows: fluorescence mode with excitation 760 nm and emission 830 nm; exposure time 5 sec; F/stop: 2 and pixel 2×2. Images collected were then processed using the Carestream MI imaging software to equally adjusted minima and maxima scale.

Results

Figure 15:
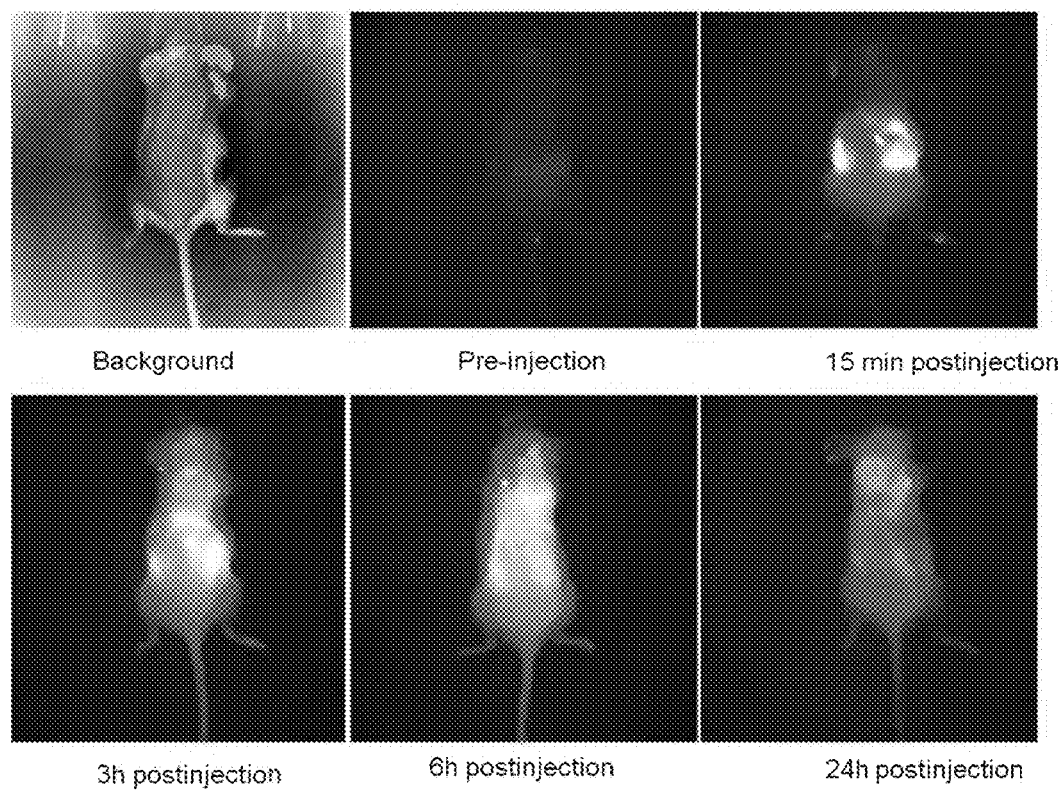
FIG. 15 shows time-dependent in vivo images of fluorescence emission from BALB/c mice bearing colon-26 tumor cells before and after treatment with SBDPiR790.

All mice received 2.5 μmol/kg of SBDPiR790 (MW=636.11 g/mol) solution in PBS (0.2 ml) via i.p. injection. Images were taken at 0 (before), 15 minutes, 3, 6, and 24 hours postinjection. SBDPiR790 showed relatively clear images with time-dependent manner (FIG. 15). At 15 minutes, it seemed the most of the dye still remained in the peritoneal cavity. At 3 hours, all skin area showed relatively bright emission with intense bright spots in mid-body (presumably kidney or peritoneal cavity). At 6 hours, most of skin area showed some emission but an intense emission was observed in the tumor area. At 24 hours, skin showed lower emission intensity than at 3 and 6 h time points but brighter emission was observed at the tumor site than other body. These results clearly demonstrate the use of SBDPiR790 for NIR in vivo optical imaging. Particularly SBDPiR790 can be a practical alternative to the sole clinically approved NIR probe, ICG. The stability, and excellent photophysical properties of SBDPiR790 and its lipophilic character make it useful for varied applications including cancer diagnosis and neurological imaging taking advantage of its ability to cross the blood-brain barrier.

Functionalization of NIR BODIPY Derivatives and Biological Evaluation

The use of molecular probes and photonic agents for in vivo therapy requires high selectivity or specificity to the diseased site. Although second generation fluorescent probes and PDT agents relied on passive targeting of tumor vasculature, not all diseased locations can take advantage of this targeting approach. Moreover, destruction of central tumor vasculature by some second generation PS though effective cannot be used for peripheral vasculature. Active targeting has become a useful tool to enhance target specificity. Active targeting involves the covalent conjugation of probes to targeting vectors such as ligands, peptides, and antibodies to improve the affinity of these probes to target sites based on corresponding receptors or antigens. Among the several targeted therapies the use of monoclonal antibodies (mAb) has received greatest attention with the FDA approval of ~25 mAb therapeutics.

The conjugation of these targeting biomolecules to PSs or fluorescent probes requires appropriate functional groups on the PS/probes. The challenges with most NIR absorbing chromophores include high hydrophobicity and limited potential for functionalization. In certain embodiments of the present disclosure, NIR BODIPY derivatives were functionalized by a meso-functionalized approach (Example 7) and extended functionalization from a modified BODIPY core (Example 8).

Figure 16:
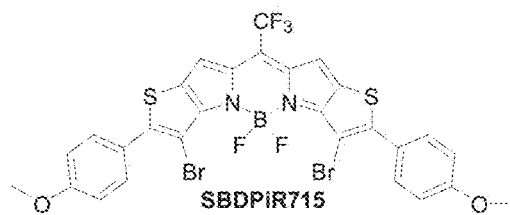
FIG. 16 shows the formula for SBDPiR715.

A BODIPY analog, SBDPiR715 (FIG. 16), showed excellent photophysical properties, balanced fluorescence emission, and effective singlet oxygen generation, as a dual functioning PS for theranostic application (PDD guided PDT). Pilot in vivo studies were performed with SBDPiR715 to gauge its potential as a dual-functioning PS. SBDPiR715 showed bright in vivo images and ablation of large tumors. However, it is highly lipophilic and planar and readily forms aggregates. SBDPiR715 was therefore functionalized with carboxylic acid moieties to increase water solubility and reduce the aggregation tendency. The dicarboxyl group functionalized SBDPiR715 can also be used for further modifications such as conjugation to delivery vectors via an ester bond.

Example 7

Synthesis of a Meso-Functionalized NIR BODIPY Derivative

A meso-functionalized NIR BODIPY derivative, 2,8-Di (4-Methoxy-phenyl)-11-benzoic acid methyl ester-dithieno [2,3-b]-[3,2-g]-5,5-difluoro-5-bora-3a,4a-diaza-s-indacene (compound 50), was created (FIG. 16) by adding a carboxy phenyl group at the meso position of a thiophene-fused BODIPY core. The synthesis utilized a previous approach to build a modified fused pyrrole substrate (see FIG. 2). A pyrrole substrate 47A was decarboxylated under thermal, copper catalyzed conditions to obtain free pyrrole at the 2-position (Compound 48). Mono methyl-terephthalate 49 was activated using thionyl chloride to generate a reactive electrophile for condensation with the modified free pyrrole (48). A subsequent boron chelation step was performed which afforded the target compound 50.

Figure 17:
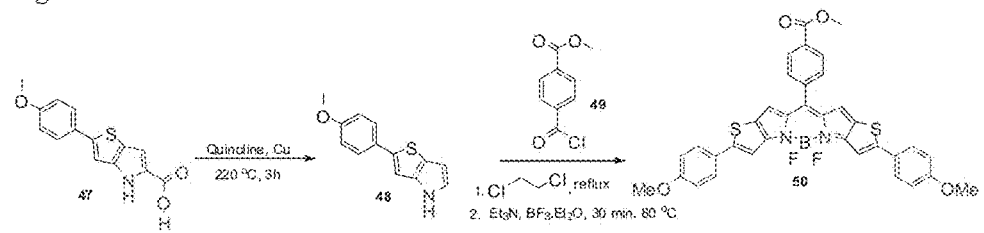
FIG. 17 shows a scheme for synthesis of a meso-functionalized NIR BODIPY derivative, Compound 50.

The synthesis of compound 50 required the preparation of the pyrrole, methoxyphenylthienopyrrole, compound 48 (FIG. 17) A basic decarboxylation approach using NaOH in ethylene glycol as well as acid promoted decarboxylation with TFA generated very low yields (<10%). Other decarboxylation methods such as transition-metal catalyzed decarboxylation often used for phenyl-substituted carboxylic acids proved unsuccessful. However, the use of doubly distilled quinoline and copper (I) oxide at high temperatures of 220° C. as reported in literature obtained an improved yield of 40%. The compound was carefully handled as it was exposed to minimal amount of light. The purification was done using a modified (1% TEA) silica-gel column chromatography. The final functionalized BODIPY bearing a phenyl carboxylate at the meso-position (50) was achieved by using the reactive 4-chlorocarbonyl-benzoic acid methyl ester (49) and the methoxyphenylthienopyrrole, (48). The reaction followed a synthetic protocol used by Burgess et al. giving similar reaction yields (3%).

Reaction conditions to obtain compound 48 (2-(4-Methoxy-phenyl)-4H-thieno[3,2-b]pyrrole: 2-(4-Methoxy-phenyl)-4H-thieno[3,2-b]pyrrole-5-carboxylic acid (compound 47) (0.50 g, 1.8 mmol), Cu powder (0.18 g, 1.3 mmol) was dissolved in doubly distilled quinoline (10 ml) and refluxed at 220° C. for 3 hours. The reaction mixture was cooled to room temperature, and the copper was filtered out. The filtrate was poured into cold water and acidified with 2 N HCl to pH 4. The solution was extracted with ethyl acetate, washed with 10% HCl, 10% NaHCO₃, brine, and water. The solution was dried over anhydrous Na₂SO₄ and evaporated to dryness. The mixture was purified by silica-gel column modified with 1% triethylamine using CH₂Cl₂ as eluent to afford a yellowish-grey solid (164 mg, 40% [based on ¹H-NMR]). ¹H-NMR (CD₂Cl₂, 300 MHz): δ 8.5 (bs, 1H), 7.57 (d, J=9.0 Hz, 2H), 7.18 (s, 1H), 6.87 (d, J=9.0 Hz, 2H), 3.89 (s, 3H) HRMS EI (m/z): Calculated for C₁₃H₁₁NOS: 229.0561. found: 229.0532 [M]⁺

Reaction conditions to obtain compound 49 (4-Chlorocarbonyl-benzoic acid methyl ester): Terephthalic acid monomethyl ester (0.25 g, 1.4 mmol) was dissolved in thionyl chloride (5 ml) and refluxed for 1 hour. Excess thionyl chloride was removed in vacuo to give an off-white solid. The solid was dissolved in anhydrous benzene (7 ml), and the solvent was evaporated. The procedure was repeated 3 times, and the solid was dried at high temperatures to remove residual solvent. 273 mg was obtained at 93% yield.

Reaction conditions to obtain compound 50 (2,8-Di(4-Methoxy-phenyl)-11-benzoic acid methyl ester-dithieno[2,3-b]-[3,2-g]-5,5-difluoro-5-bora-3a,4a-diaza-s-indacene): Compounds 48 (0.16 g, 0.7 mmol) and 49 (0.07 g, 0.4 mmol) were dissolved in 1,2-dichloroethane, and the solution was refluxed for 72 hours. The solution was cooled to room temperature, and TEA and boron trifluoride etherate was added. The mixture was refluxed for 30 minutes under He (g) atmosphere. The solution was washed with water and brine, and the residue was purified by silica-gel column chromatography using ethyl acetate-toluene (5:95) as eluent. A green solid was obtained (5 mg, 3%, [based on $^1$H-NMR]). $^1$H-NMR (CDCl$_3$, 300 MHz): δ 8.12 (d, J=9.0 Hz, 2H), 7.60 (d, J=9.0 Hz, 4H), 7.44 (d, J=9.0 Hz, 2H), 7.41 (s, 2H), 6.88 (d, J=9.0 Hz, 4H), 6.67 (s, 2H), 3.80 (s, 3H), 3.92 (s, 6H). HRMS EI (m/z): Calculated for $C_{35}H_{25}BF_2N_2O_4S_2$: 650.1317. found: 650.1321 [M]$^+$.

Optical Properties of Compound 50

Figure 18:
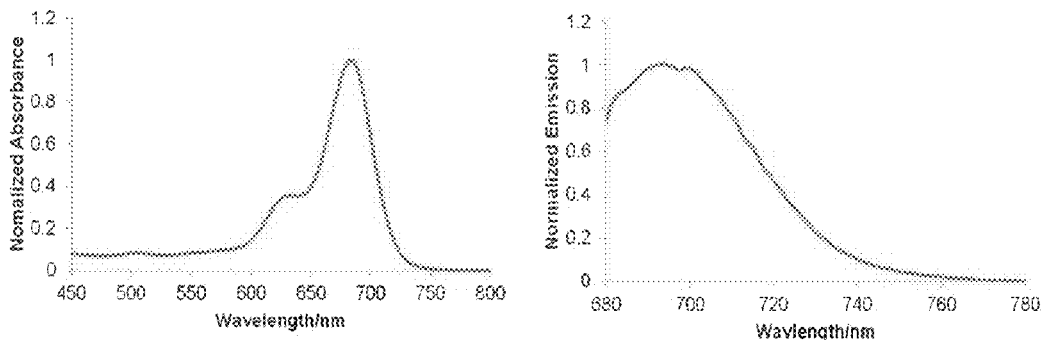
FIG. 18 depicts optical spectra of the meso-functionalized NIR BODIPY derivative, Compound 50.

The solution of 50 in CHCl$_3$ gave a vivid bluish-green color and accounted for a strong 0-0 absorption at 685 nm. The molar extinction coefficient was remarkably lower (85 000 M$^{-1}$ cm$^{-1}$) than the CF$_3$ meso substituted analogues (~200 000 M$^{-1}$ cm$^{-1}$). That could be attributed to the free rotation of the phenyl carboxylate ring at the meso-position to the fluorophore that broke the planarity of the structure. In addition, the free rotation accounts for the relatively low fluorescence. Absorbance and emission spectra of compound 50 are shown in FIG. 18.

Example 8

Synthesis of a Di-Carboxylic Acid Functionalized SBDPiR

Figure 19:
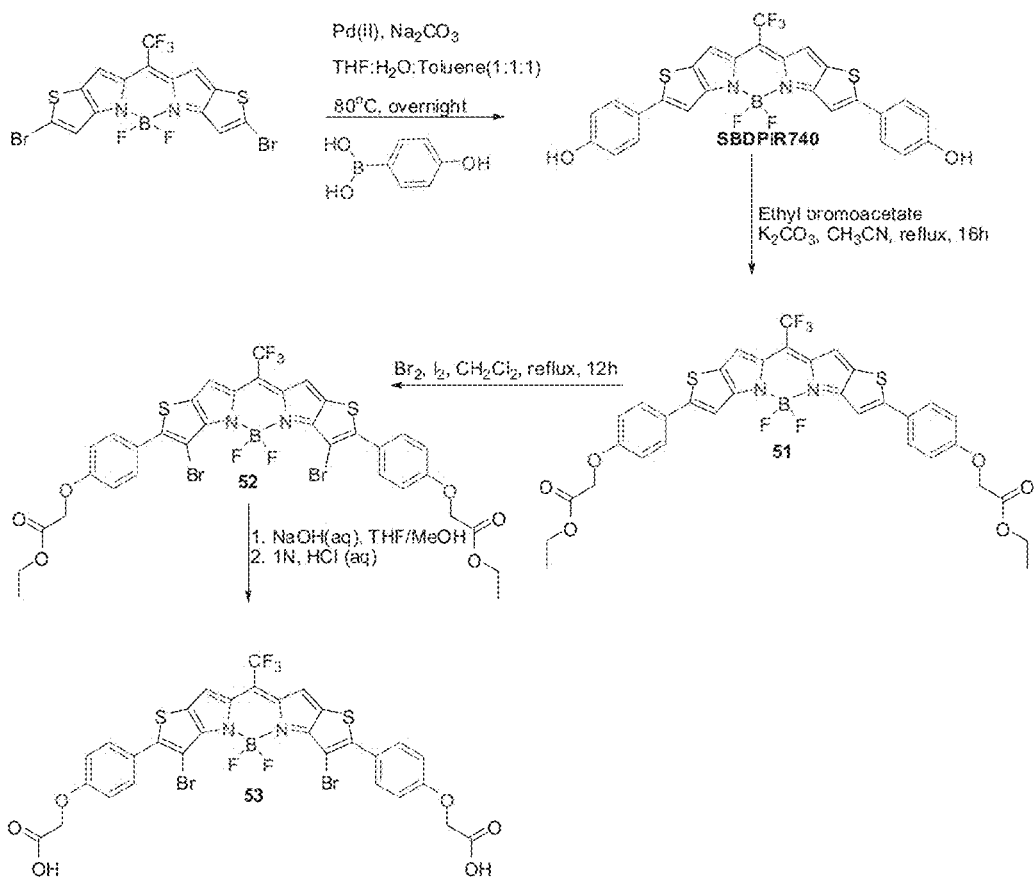
FIG. 19 shows a scheme for the synthesis of a functionalized NIR BODIPY derivative, Compound 53.

Formation of the di-carboxylic acid BDP635 analog, compound 53, provided a derivative with improved water solubility and reduced aggregation tendency compared to a more planar compound. In addition, the carboxylic acid groups provide attachment sites for the conjugation to delivery vectors or delivery vehicles. SBDPiR740 (see FIG. 6 and Example 2) was treated with ethylbromoacetate in a substitution reaction to form compound 51, which was brominated to form compound 52, which was then subjected to basic hydrolysis to convert the ester groups of 52 to a pair of free carboxylic acids groups in compound 53 (FIG. 19).

Reaction conditions to obtain compound 51 (2,8-Di(4-Ethoxycarbonylmethoxy-phenyl)-11-trifluoromethyl-dithieno[2,3-b]-[3,2-g]-5,5-difluoro-5-bora-3a,4a-diaza-s-indacene): SBDPiR740 (0.10 g, 0.2 mmol), ethylbromoacetate (0.12 g, 0.7 mmol) and K$_2$CO$_3$ (0.05, 0.4 mmol) were dissolved in anhydrous CH$_3$CN under N$_2$ atmosphere. The solution was heated at 80° C. for 16 hours. After the complete consumption of the starting material (monitored by TLC), the reaction was stopped. The solvent was removed, and the residue was dissolved in CH$_2$Cl$_2$. The resulting solution was washed with water and dried over anhydrous Na$_2$SO$_4$. The mixture was purified by recrystallization from ethyl acetate/cyclohexane mixture to afford a green solid (91 mg, 70% [based on $^1$H-NMR]). $^1$H-NMR (CDCl$_3$, 300 MHz) δ: 7.67 (d, J=9.0 Hz, 4H), 7.48 (s, 2H), 7.32 (s, 2H), 6.97 (d, J=9.0 Hz, 4H), 4.70 (s, 4H), 4.27 (q, J=7.1 Hz, 4H), 1.30 (t, J=7.1 Hz, 6H) HRMS EI (nm/z): Calculated for $C_{34}H_{24}BBr_2F_5N_2O_6S_2$: 728.1245. found: 728.1227 [M]$^+$.

Reaction conditions to obtain compound 52 (3,7-Dibromo-2,8-di(4-Ethoxycarbonylmethoxy-phenyl)-11-trifluoromethyl-dithieno[2,3-b]-[3,2-g]-5,5-difluoro-5-bora-3a,4a-diaza-s-indacene: Compound 51 (0.07 g, 0.1 mmol) along with I$_2$ (0.001 g) was dissolved in CH$_2$Cl$_2$ (15 ml). A solution of Br$_2$ (0.04 g, 0.3 mmol) in CH$_2$Cl$_2$ (5 ml) was added dropwise and stirred at 40° C. for 12 hours. The reaction mixture was neutralized with aqueous Na$_2$CO$_3$ solution, and the aqueous layer was separated from the organic layer. The aqueous layer was further extracted with diethyl ether, the combined organic layers were dried over anhydrous Na$_2$SO$_4$ and the solvents were removed by evaporation to obtain a brown solid (40 mg, 52% [based on $^1$H-NMR]). $^1$H-NMR (CD$_2$Cl$_2$, 300 MHz) δ: 7.73 (d, J=9.0 Hz, 4H), 7.40 (s, 2H), 7.01 (d, J=9.0 Hz, 4H), 4.70 (s, 4H), 4.25 (q, J=7.1 Hz, 4H), 1.30 (t, J=7.1 Hz, 6H) HRMS EI (m/z): Calculated for $C_{34}H_{24}BBr_2F_5N_2O_6S_2$: 885.9435. found: 885.9419 [M]$^+$.

Reaction conditions to obtain compound 53 (3,7-Dibromo-2,8-di(4-Carboxymethoxy-phenyl)-11-trifluoromethyl-dithieno[2,3-b]-[3,2-g]-5,5-difluoro-5-bora-3a,4a-diaza-s-indacene): Compound 52 (0.04 g, 0.04 mmol) was dissolved in a 1:1 mixture of THF/MeOH, and 0.4 N NaOH (aq.) was added. The reaction was refluxed for 2 hours. The THF/MeOH was removed under vacuum, diluted with water, and acidified with 1N HCl. The precipitate was filtered and dried (23 mg, 63% [based on $^1$H-NMR]). $^1$H-NMR (CD$_2$Cl$_2$, 300 MHz) δ: 7.73 (d, J=9.0 Hz, 4H), 7.40 (s, 2H), 7.01 (d, J=9.0 Hz, 4H), 4.70 (s, 4H) HRMS EI (nm/z): Calculated for $C_{34}H_{24}BBr_2F_5N_2O_6S_2$: 829.8809. found: 829.8819 [M]$^+$.

Figure 20:
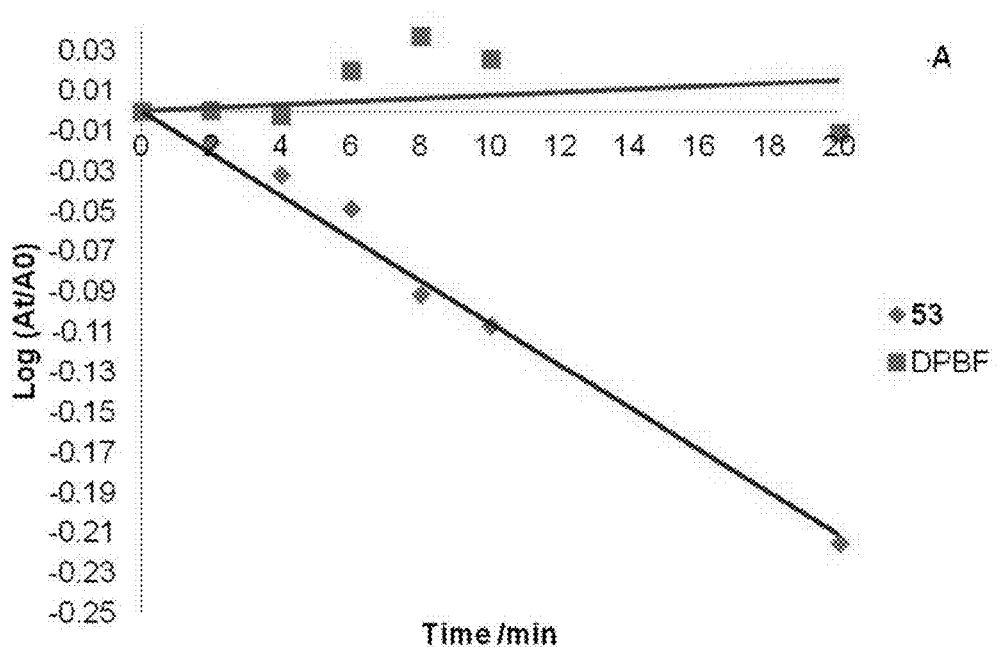
FIG. 20 is a graph showing comparative SO generation by 1,3-diphenylisobenzofuran (DPBF) and Compound 53.
Figure 21:
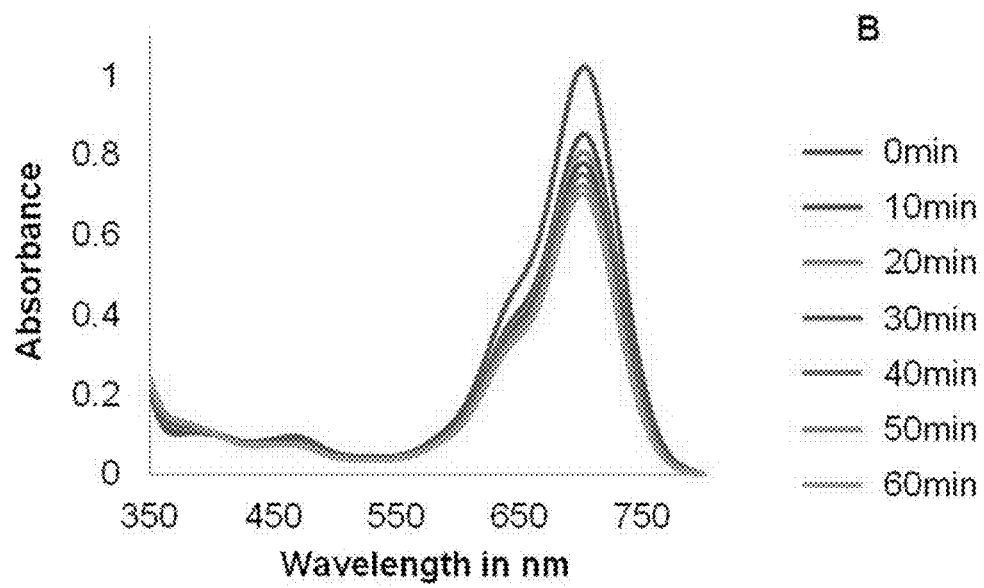
FIG. 21 is a graph showing the photostability of compound 53.

Singlet oxygen generation and photostability: A singlet oxygen generation experiment on compound 53 using the indirect method of DPBF photooxidation was performed. There were strong similarities of the behavior of 53 towards DPBF with SBDPiR715. In addition, the photostability of 53 showed relatively better than the clinically approved m-THPC (Foscan). It was established that the functionalization of these novel PSs does not affect their excellent photophysical behavior (FIG. 20). The photooxidation of DPBF was monitored by UV-vis spectrophotometer at 410 nm. Within 20 minutes the oxidation rate compared to that of SBDPiR715, indicating that compound 53 is also a potent singlet oxygen generator despite the functionalization. Additionally, less than 30% of 53 photobleached under the harsh light illumination condition over a period of an hour, which is a strong evidence for photostability (FIG. 21).

Example 9

In Vivo Optical Imaging with Compound 53

Optical imaging was performed with an IVIS Spectrum small-animal in vivo imaging system (Caliper LS). The Living Image Software v3.0 (Caliper LS) was used to analyze images and measurements of fluorescent signals. Excitation and emission wavelengths of 720 nm and 760 nm, respectively, were used to acquire in vivo fluorescent images of Compound 53 (M.W=830.20 μmol). All images were attained using a 1-s exposure time and an f/stop of 1, with a sampling of multiple angles with animal under Isoflurane anaesthesia. Animals were injected with 2.5 μmol/kg (2 mg/kg) of 53 via i.p. administration.

Figure 22:
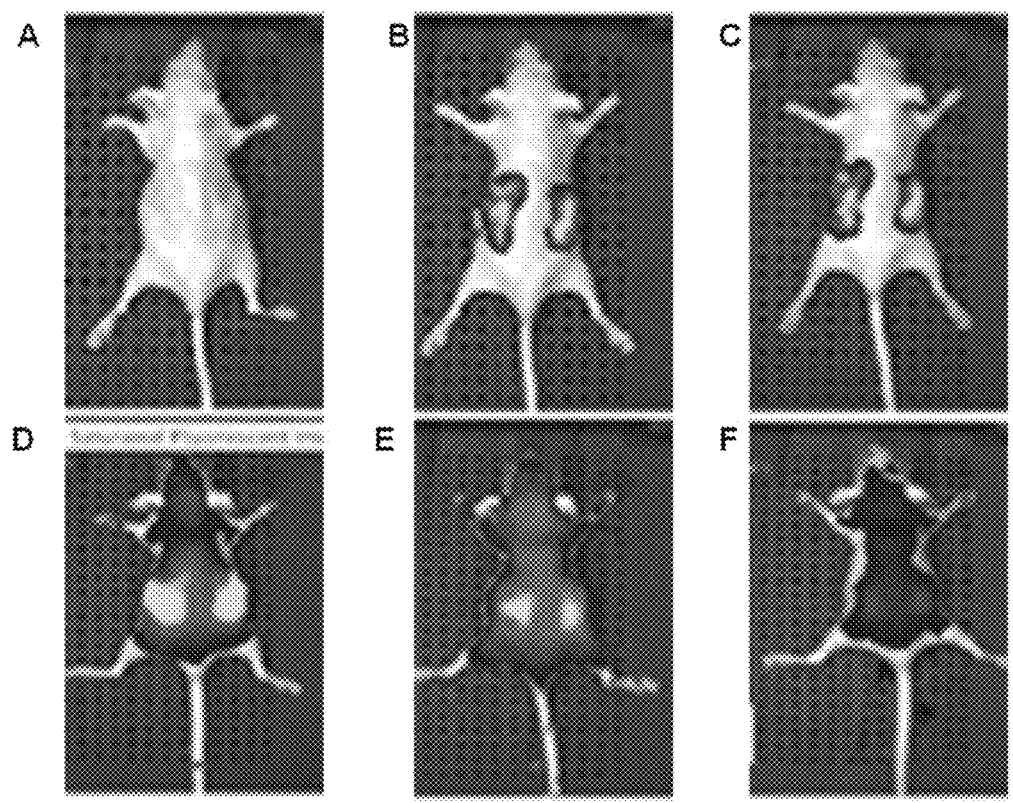
FIG. 22 shows fluorescent images of nude mice treated with Compound 53 (from top left: (A) time 0, (B) 5 minutes, (C) 10 minutes, (D) 3 hours, (E) 6 hours, and (F) 12 hours after i.p. injection).

The in vivo imaging study of compound 53 proved its effectiveness as an in vivo optical imaging probe. Bright fluorescence signals were detected from mice (FIG. 22). At 5 and 10 minutes, two bright areas were observed in the mid-body, presumably due to the PS in peritoneal cavity before absorption to the circulatory system (blood). At 3 hours and 6 hours, most skin showed bright emission, and two clear bright spots were also observed, probably kidneys. At 12 hours, the intensity of skin was lower than the 3 hour and 6 hour images. Most of the compound 53 might have been cleared from the system.

Example 10

In Vivo Biodistribution and PDT of SBDPiR715

PS: To obtain an injection solution of SBDPiR715, the emulsifier Tween 80 was used. Tween 80 is a nonionic surfactant, frequently used in vivo as a solubilizing agent for highly lipophilic therapeutics. The formulation procedure required dissolving the PS in a minimal amount of Tween 80 (100 μl). The paste was allowed to stand overnight. 5% Dextrose in phosphate-buffered saline (PBS) solution was added, and the solution was sonicated for 1 hour. The resulting green solution was filtered through a 0.2 μm membrane filter. To ensure the accuracy of the concentration, which might vary due to partial solubility of the PS, the exact concentration was confirmed by UV-visible spectral analysis of the solutions prior to dosing.

Cells and Animal Models: Colon-26 mouse carcinoma cells were obtained from the American Type Culture Collection (ATCC) and cultured in minimum essential medium supplemented with 10% (v/v) fetal calf serum (FCS), 50 U ml$^{-1}$ penicillin, 50 μg ml$^{-1}$ streptomycin, and 1% (v/v) L-glutamine. The cells were maintained in 5% $CO_2$ (v/v) and 21% $O_2$ (v/v) at 37° C. All animal experiments were approved by IACUC of the University of Oklahoma Health Sciences Center. Female BALB/c mice were received from Charles River at 6-8 weeks old. Balb/c mice were shaved on the upper back and depilated with Nair (Carter-Wallace Inc., New York, N.Y., USA). Mice were anesthetized with an i.p. injection of ketamine/xylazine cocktail (90 mg kg$^{-1}$ ketamine and 10 mg kg xylazine). One million colon-26 cells were injected subcutaneously in one dorsal neck area suspended in 100 ml PBS. Tumors grew predictably in all the mice and reached a size of 4- to 6-mm diameter in 5-7 days, or 8-11 mm in 14-16 days after injection, at which time they were used for PDT.

Drug Efficacy Studies: PDT Protocol

SBDPiR715 in 1% Tween 80-5% Dextrose solvent was injected i.p. at a dose of 3 μmol/kg (2.2 mg/kg) and 5 μmol/kg (3.7 mg/kg) in 0.2 ml solution. Tumors were irradiated 6 hours, 24 hours, or 32 hours after the injection using a Lumacare LC-122M with a fiber-optic light delivery system (Lumacare, Newport Beach, Calif., USA) emitting light at 700 nm (±40 nm). The illuminating spot had a diameter of 1.2 cm and was positioned so that the entire tumor and a surrounding 2-3 mm area of normal tissue were exposed to light. No evident temperature increase was detected at the site of irradiation. Mice were anesthetized as described above, and the tumor-bearing limb was positioned under the spot. Total dose of 200-300 mW/cm$^2$ was delivered for 30 minutes (360-540 J cm$^{-2}$). Mice bearing colon-26 tumors were also irradiated without having received injection of SBDPiR715. Another group of animals was treated with SBDPiR715 i.p. without irradiation. After irradiation, mice were allowed to recover in an animal cotton blanket until they resumed normal activity. A positive tumor response was ascribed to tumors that appeared flat blackened or reddened scarp and necrotic tissue within a few days after PDT. Animals were considered cured after complete tumor regression and the absence of a palpable tumor.

A mass tumor necrosis was observable after a few hours—a day following PDT treatment with the development of necrosis and eschar. Tumor healing, however, took ~30 days with remodeling of the damaged or scarred tissue. The protocol treated larger tumors (8-11 mm diameter) that are rarely used pre-clinically. No weight loss or other visual signs of toxicity was observed at the treatment dose of 5 μmol/kg (3.7 mg/kg). There was no effect on the group treated with light alone.

Drug Biodistribution

Mice were injected via i.p. with SBDPiR715 (5 μmol/kg/3.7 mg/kg). After 24 hours postinjection, the mice (n=3) were euthanized by $CO_2$ inhalation. Tissues were excised from major organs and tumor. Collected tissues were rinsed with PBS and blotted dry. One hundred milligram of excised tissue was homogenized with $CHCl_3$ (1 ml). The homogenates were centrifuged at 5160 g for 20 minutes, and the supernatant was used for fluorescence measurement (excitation at 710 nm and emission at 754 nm). The amount of compound in each sample was evaluated relative to the standard curve and expressed in "mg/g of tissue" unit.

Results

Figure 23:
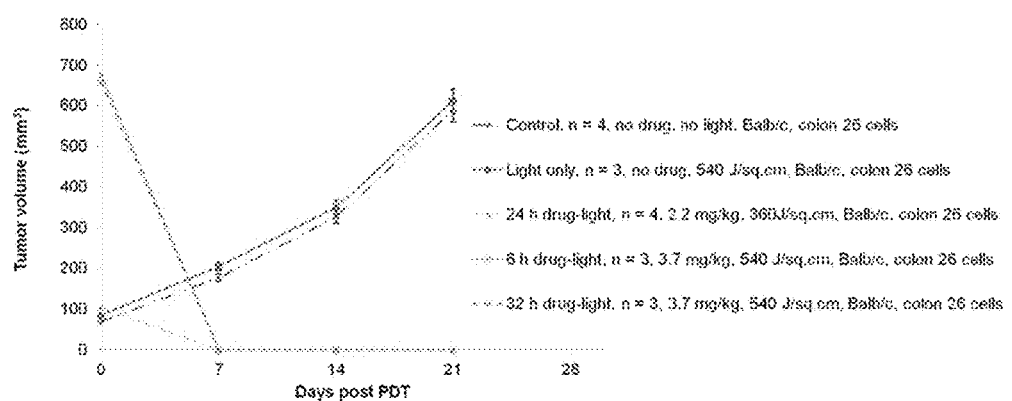
FIG. 23 is a graph showing in vivo responses to SBDPiR715-mediated PDT (standard error of mean used) in Balb/c mice injected with colon-26 cells.

The SBDPiR715-mediated PDT studies conducted under varying drug-light interval of 6 h (n=3), 24 h (n=4) and 32 h (n=3), respectively (FIG. 23), is demonstrated herein to have use as a phototherapeutic agent. The in vivo response to SBDPiR715 PDT used the colon-26 tumor bearing mice to determine drug-light combination tolerance. Two approaches were used in the treatment: (1) traditional PDT protocol used with a 24 h drug-light interval with a starting tumor size of ~85 mm$^3$, and (2) treatment of larger tumor sizes (~650 mm$^3$) with 6 hour and 32 hour drug-light interval for preferential drug accumulation at the tumor site.

Figure 24:
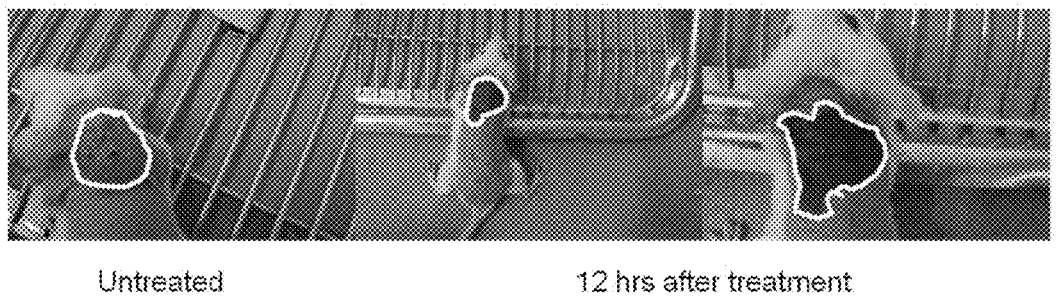
FIG. 24 shows in vivo images of the response to SBDPiR715-mediated PDT using 6 hour drug-light interval (white line→tumor [untreated] and necrotic [treated] boundary) in Balb/c mice injected with colon-26 cells.
Figure 25:
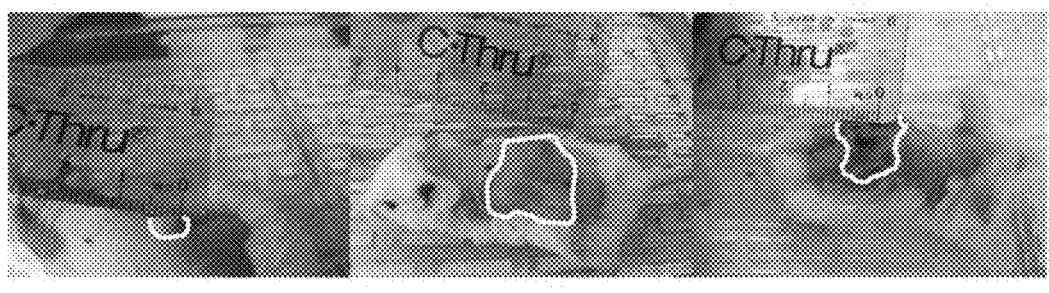
FIG. 25 shows in vivo images of the response to SBDPiR715-mediated PDT using 24 hour drug-light intervals (white line→tumor [untreated] and necrotic [treated] boundary) in Balb/c mice injected with colon-26 cells.
Figure 26:
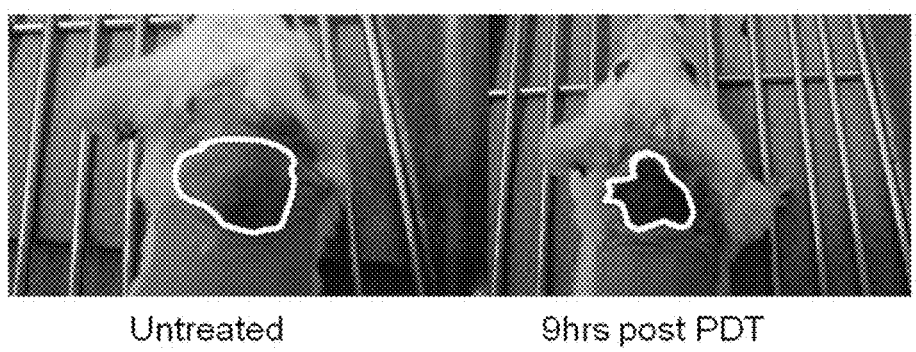
FIG. 26 shows in vivo images of the response to SBD-PiR715-mediated PDT using 32 hour drug-light interval (white line→tumor [untreated] and necrotic [treated] boundary) in Balb/c mice injected with colon-26 cells.

Within 3 weeks control groups of tumor alone (control, n=4) and tumor with 24 hour drug-light interval (light only, n=3) reached high tumor volumes at consistent rates. In the same period, the treatment groups experienced mass necrosis and eschar within a day. For the 6 and 24 hour drug-light interval treatment groups, the observed necrosis spread to neighboring skin regions probably due to SBDPiR715 in the skin causing skin photosensitization (FIG. 24 and FIG. 25). In the 32 hour treatment group, there seemed to be a preferential accumulation of the drug in the tumor region leading to a confinement of necrosis to the tumor region (FIG. 26). All the treatment groups showed complete tumor ablation as monitored for 90 days.

This example shows SBDPiR715 was well tolerated with high efficacy in vivo employing short to long drug-light intervals. The observed cure in the colon-26 bearing tumor model and in two treatment groups larger than clinical tumor sizes is encouraging. In addition, the in vivo response of SBDPiR715 compares well to the established aza-BODIPY, azadipyrromethane (ADPM06), for preclinical indication as well as the vascular targeting TOOKAD developed in 2002 and in current clinical trials for prostate cancer.

Figure 27:
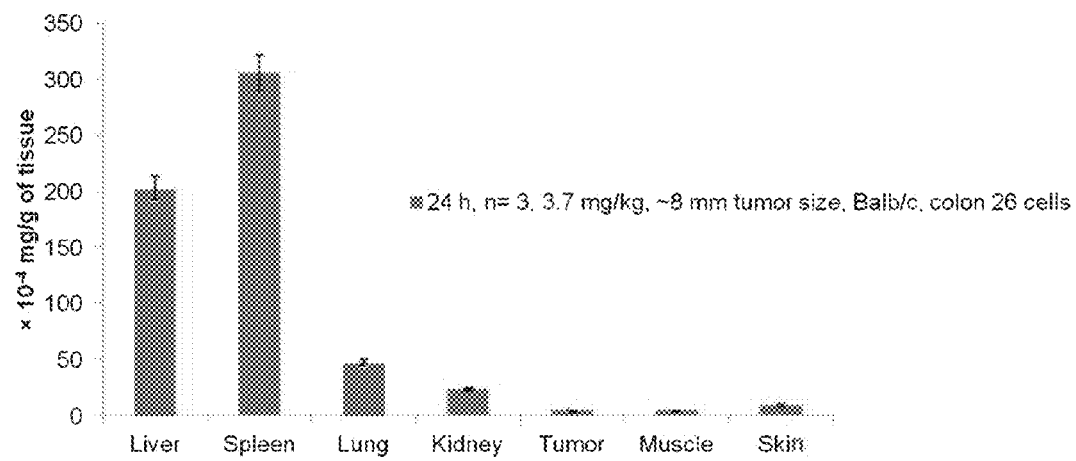
FIG. 27 is a graph showing the biodistribution of SBD-PiR715 in organs of in Balb/c mice injected with colon-26 cells (Standard deviation used).

SBDPiR715 has an organ biodistribution pattern (FIG. 27) consistent with a wide range of PSs. The innate fluorescence property of SBDPiR715 enabled its biodistribution in various organs after systemic delivery intraperitoneally. In the biodistribution study, a higher accumulation of SBDPiR715 was observed in the liver and spleen. The observation might be as a result of the general knowledge of hydrophobic agent's elimination from an organism through the bile-gut pathway. The high content of LDL receptors in the liver, spleen, and kidney might influence the result, as SBDPiR715 is hydrophobic.

Example 11

In Vivo PDT Response Following SBDPiR690 Treatment

The non-invasive diagnosis and therapy of disease indications with light is an emerging therapeutic modality. Fluorescence imaging and PDT have been established as reliable prognosis and disease treatments, particularly for cancer and other malignancies. Additional clinically effective fluorophores and PSs which absorb and emit in the NIR region are needed. More specifically, dyes absorbing >700 nm with inherent excellent photophysical properties are desired. These properties can include, but are not limited to, one or more of: (1) high photostability, (2) sharp absorption and emission bands, (3) high molar extinction coefficient, (4) appreciable fluorescence quantum yield/singlet oxygen quantum yield, and (5) potential for functionalization.

Figure 28:
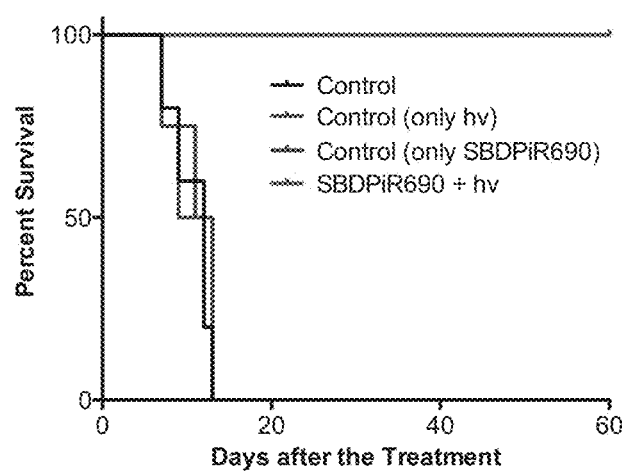
FIG. 28 shows percent of survival of control and treated Balb/c mice injected with colon-26 cells. Photodynamic therapy treatment with SBDPiR690-induced PDT resulted in 100% survival after 60 days compared to 100% mortality of control mice within less than 20 days. Percent survival and average tumor volume.
Figure 29:
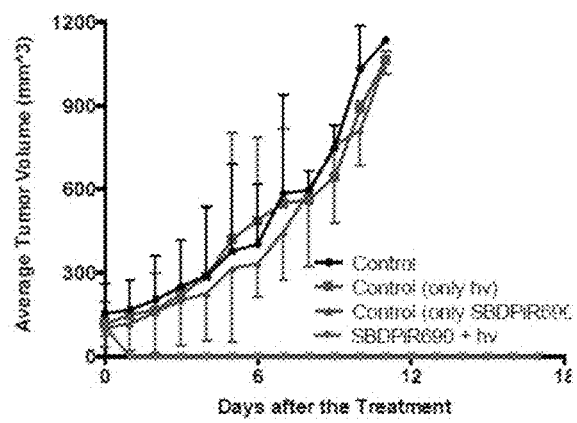
FIG. 29 shows tumor volume of control and treated Balb/c mice injected with colon-26 cells. Photodynamic therapy treatment with SBDPiR690-induced PDT resulted in elimination of tumors compared to average tumor volume of 900-1200 mm$^3$ within 11 days in control animals.

In this example, treatment of Balb/c tumor bearing mice with SBDPiR690 demonstrated therapeutic efficacy in vivo. 25 animals were divided into 4 groups: control, dark control (SBDPiR690 only), light control (light only), and SBDPiR690-with light exposure (PDT). SBDPiR690 was intravenously injected into mice with colon-26 tumor model, followed by light illumination after 15 minutes postinjection using a light dose of 100 mW/cm$^2$ (FIGS. 28-29). Mice body weight and tumor response at high light doses (~500 J cm$^{-2}$) were used for initial toxicity profiles. Body weight was fairly constant even at high intensity light doses. Mass necrosis localized at the tumor region was evident after 24-72 h using an optimal light fluence of 150 J cm$^{-2}$. An associated oedema and inflammation was observable after 24 hours, but healed after a few days. Mice were pronounced cured after tissue remodeling, with no palpable tumor observed even after 60 days post-treatment.

The high success rate associated with anti-vascular PDT treatment with SBDPiR690 in comparison with the standard PDT protocol of photosensitizer accumulation over ~24 h before light illumination is due to the synergistic benefits of the vascular targeting treatment protocol. There was a high blood oxygen level at the vascular regions relative to surrounding tissue, and in addition, photosensitizers were in maximal concentrations in the blood shortly after drug administration; these are indicators of effective PDT results. Moreover, photosensitizer compounds readily have access to vascular endothelial cells in the blood. Overall, effective photosensitizer distribution to tumor regions as induced by vascular rupture and hemorrhage formation overshadows the approach of diffusion across the capillary walls. Blood stasis induces necrosis and subsequent tumor eradication, and that is a result of oxygen and nutrient deprivation during illumination after short drug administration.

Effect of PDT Treatments on Tumor Environment

Figure 30:
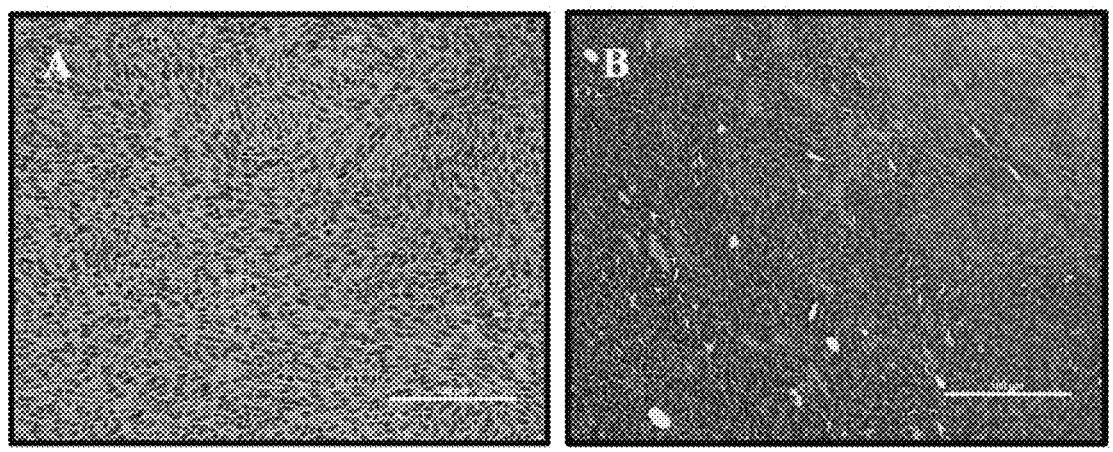
FIG. 30 shows micrographs of H & E stained colon cancer tumors from treated and untreated Balb/c mice (A) Control; no drug, without light irradiation, (B) Treatment; SBD-PiR690 and light irradiation.

To access the effect of SBDPiR690 on the tumor regions, tumor samples were collected from SBDPiR690 treated and control mice 1 day post treatment. The samples were fixed, embedded, sectioned, and stained using hematoxylin and eosin. The H&E stained tissue showed distinct differences in tissue morphology between treated and untreated groups with characteristic demonstration of necrosis associated with the treated mice (FIG. 30).

These results demonstrated the effectiveness of the novel compound, SBDPiR690, a NIR non-halogenated BODIPY, in imparting a therapeutic response in mice bearing tumors. The inherent fluorescent properties of SBDPiR690 enabled its use in real time whole body imaging to evaluate the clearance and biodistribution of the drug in organs, making it an applicable theranostic agent. The drug clears from organs and tissue by 24 hours, reducing the occurrence of skin photo-toxicity, which is a major problem among photosensitizers. Histology studies further demonstrate significant differences in tissue morphology owing to necrosis after treatment. These findings show the effectiveness of SBDPiR690 as a photosensitizer for use in PDT in clinical setting.

The work described herein was focused mainly on the synthesis of NIR BODIPY dyes to: (1) provide improved photodynamic response and (2) generate efficient fluorophores for fluorescence imaging. The biological function of these novel classes of NIR BODIPY was explored for in vivo photodynamic response to ablate tumors and in vivo optical imaging for monitoring and diagnosis.

The derivatives described herein show strong absorption in the NIR from 720-766 nm in CHCl$_3$ and strong emission of 738-820 nm. The sulfur-containing analogues showed appreciable singlet oxygen generation comparable to the core-modified porphyrins, which is a well-studied class of chromophores. Photobleaching kinetics showed the high photostability of these NIR BODIPY derivatives in comparison to m-THPC (a clinically approved PDT agent) and its NIR analogue m-THPBC. Novel embodiments described herein provide compounds with appreciable fluorescence quantum yield that can be used as a dual-functional agent for PDT and diagnosis or for fluorescence-guided PDT.

The presently disclosed inventive concepts include compounds having a propensity towards functionalization. SBDPiRs with good optical absorption in the NIR from 650-840 nm were successfully synthesized. Nucleophilic substitution of substituted phenols and thiophenols was used to generate SBDPiRs with excitability 650-700 nm. Suzuki and Stille coupling was used to generate SBDPiRs with excitability 688-740 nm, and the Heck coupling was used to obtain SBDPiRs with 755-786 nm excitability. The study indicated a viable alternative to the cynanines and phthalocyanines with the NIR absorption and high molar extinction coefficient of the SBDPiRs. Finally, the functionalization of these NIR BODIPY derivatives and their biological application as photodynamic therapeutic agents and fluorescence imaging probes was demonstrated. Overall, the presently disclosed inventive concepts include effective NIR photodynamic agents and fluorescent probes for improved photodynamic response and fluorescence imaging in vivo.

The structural derivatization (addition of modifying groups and functionalization thereof) of the base compounds (e.g., BDP635 and other compounds based on Formula (I)) is intended to achieve near IR absorption (>650 nm), appropriate water solubility (e.g., −2<log D (or log P7.4)<4), and reduced aggregation of the compounds which are advantageous for biomedical applications. Any known methods for achieving these goals can be used. As examples, near IR absorption can be achieved by adding extended pai electron condition and adjusting the molecular dipole moment by adding electron donating or withdrawing groups. Water solubility can be improved by functionalizing the modifying groups, for example, by adding water solubilizing groups such as, but not limited to, carboxylic acid group(s), sulfonate group(s), amine groups, and PEG (polyethylene glycol) groups. Aggregation tendency can be reduced, for example, by making the whole molecule less symmetric, flexible, and/or amphiphilic. In addition, the derivation can help control the photo physical properties using ON/OFF switching groups that can be affected by certain stimuli such as, but not limited to, pH, enzyme, and light.

The BODIPY derivatives (chromophores) presently disclosed have uses including, but not limited to, in vivo imaging and PDT. For example, in cancer treatment, PDT can destroy the vasculature surrounding tumor cells, causing activation of immunological responses against them. The vascular targeted PDT described herein possesses numerous advantages in improved efficacy of treatment. The injected chromophores accumulate rapidly and in high concentrations after intravenous administration and the essential element for photochemical reaction, molecular oxygen, is readily available. Moreover, the role of the vascular network to supply oxygen and nutrients to cancer cells makes the occlusion of the vessels an effective approach to treat tumors.

Overall, this approach can be used to treat different tumor types, considering the shared biochemical and morphological properties. The derivatives preferentially accumulate in diseased tissue toward which electromagnetic radiation can be focused, causing damage to the targeted area due to singlet oxygen production by the chromophore. Cancerous conditions that can be treated with the chromophores presently disclosed include, but are not limited to, cancers of the breast, skin, lung, gastrointestinal tract (including the stomach, esophagus and colon), ovarian, urinary tract, uterus, bladder, pancreas, and prostate. Non-malignant diseased states such as age-related macular degeneration (AMD), resistant microbial infections, and atherosclerosis can also be treated with the chromophores presently disclosed. Treatment options can include adjustments (by the attending physician) in the chromophore concentrations, concentration, light intensity and duration, and oxygen availability, for example. The antivasculature effects of PDT can be facilitated by sensitizers that naturally or rationally accumulate in blood vessels and may be referred to as anti-angiogenesis agents that prevent the formation of blood vessels and growth of endothelial cells or short drug administration and light illumination intervals. The chromophores of the presently disclosed inventive concepts can be administered at dosages ranging between, for example, about 1 µg chromophore/kg of body weight to about 10 mg chromophore/kg of body weight (e.g., as administered through subcutaneous or intravenous or intramuscular injections, or other appropriate method) or at a range between any two integers in said range of 1 µg/kg to about 10 mg/kg of body weight. For example, the chromophore can be administered at a dose ranging between, for example, about 10 µg/kg to about 1000 µg/kg, or about 50 µg/kg to about 200 µg/kg. The exact amounts of the chromophore can be adjusted by the attending physician to obtain optimal therapeutic use with minimal side effects. Duration of illumination of the electromagnetic radiation can also be determined and adjusted by the attending physician to obtain optimal therapeutic use with minimal side effects.

While the presently disclosed inventive concepts have been described herein in connection with certain embodiments so that aspects thereof may be more fully understood and appreciated, it is not intended that the presently disclosed inventive concepts be limited to these particular embodiments. On the contrary, it is intended that all alternatives, modifications, and equivalents are included within the scope of the presently disclosed inventive concepts as defined herein. Thus the examples described above, which include particular embodiments, will serve to illustrate the practice of the presently disclosed inventive concepts, it being understood that the particulars shown are by way of example and for purposes of illustrative discussion of particular embodiments of the presently disclosed inventive concepts only and are presented in the cause of providing what is believed to be the most useful and readily understood description of procedures as well as of the principles and conceptual aspects of the inventive concepts. Changes may be made in the formulation of the various compositions described herein, the methods described herein or in the steps or the sequence of steps of the methods described herein without departing from the spirit and scope of the presently disclosed inventive concepts.

What is claimed is:

1. A compound represented by structural Formula (I) or a pharmaceutically acceptable salt thereof:

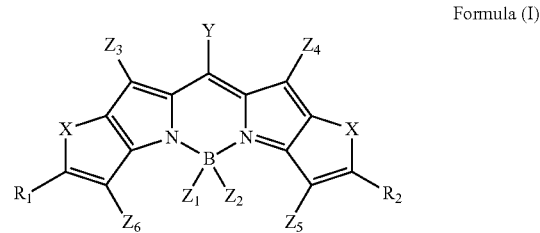

Formula (I)

wherein:

Y represents $CF_3$, $CCl_3$, $CBr_3$, $CI_3$, or $CH_3$;

X represents S, Se, or Te;

$Z_1$ and $Z_2$ are each independently selected from the group consisting of a halogen, alkyl, alkenyl, alkynyl, alkoxy, aryl, heteroaryl, heteroarylalkyl, and heteroarylalkoxy, wherein the heteroatom is O, S, or N;

$Z_3$, $Z_4$, $Z_5$, and $Z_6$ are each independently selected from the group consisting of hydrogen, a halogen, alkyl, alkenyl, alkynyl, alkoxy, aryl, heteroalkyl, heteroalkoxy, heteroaryl, heteroarylalkyl, heteroarylalkoxy, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N; and $R_1$ and $R_2$ are each independently selected from the group consisting of a halogen, alkyl, alkenyl, alkynyl, alkoxy, aryl, haloaryl, haloheteroaryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein the $R_1$ and $R_2$ groups are substituted or non-substituted.

2. The compound of claim 1, wherein each of $R_1$ and $R_2$ is independently selected from at least one of the following structures:

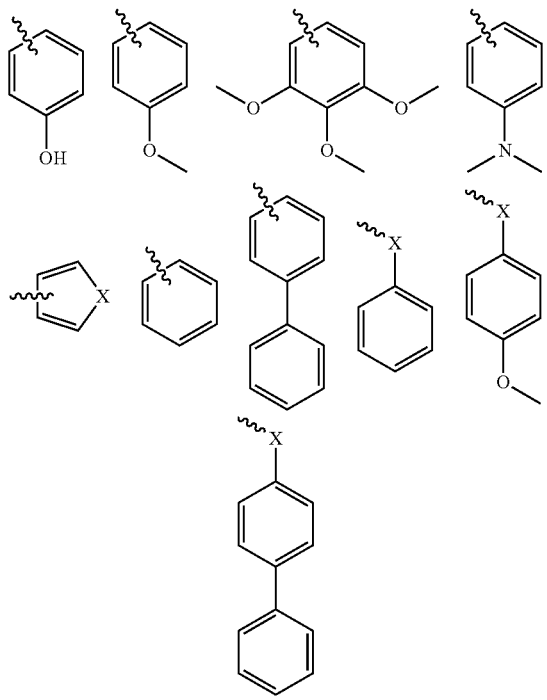

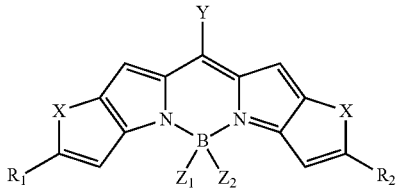

wherein X represents NH, O, or S.

3. The compound of claim 1, further defined as represented by structural Formula (II) or a pharmaceutically acceptable salt thereof:

Formula (II)

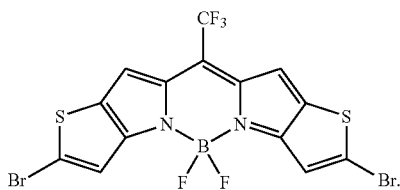

wherein:
Y represents $CF_3$, $CCl_3$, $CBr_3$, $CI_3$, or $CH_3$;
X represents S, Se, or Te;
$Z_1$ and $Z_2$ each independently represents F, Cl, Br, or I; and
$R_1$ and $R_2$ are each independently selected from the group consisting of an alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, and diarylether, diheteroarylether, combinations thereof, wherein the heteroatom is O, S, or N, and wherein the $R_1$ and $R_2$ groups are substituted or non-substituted.

4. The compound of claim 1, further defined as represented by structural Formula (III) or a pharmaceutically acceptable salt thereof:

Formula (III)

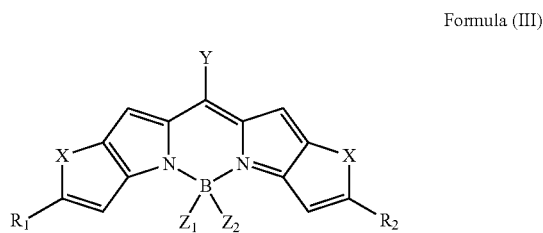

wherein:
Y represents $CF_3$, $CCl_3$, $CBr_3$, $CI_3$, or $CH_3$;
X represents S, Se, or Te;
$Z_1$ and $Z_2$ each independently represents F, Cl, Br, or I; and
$R_1$ and $R_2$ each independently represents F, Cl, Br, or I.

5. The compound of claim 4, further defined as represented by structural Formula (IV) or a pharmaceutically acceptable salt thereof:

Formula (IV)

6. The compound of claim 1, wherein:
$Z_3$-$Z_6$ are hydrogen; and
$R_1$ and $R_2$ are each independently selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein $R_1$ and/or $R_2$ are substituted or non-substituted.

7. The compound of claim 1, wherein:
at least two of $Z_3$-$Z_6$ comprise a halogen selected from the group consisting of Cl, F, Br, and I; and
$R_1$ and $R_2$ are each independently selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein $R_1$ and/or $R_2$ are substituted or non-substituted.

8. The compound of claim 1, wherein $R_1$ and $R_2$ and at least two of $Z_3$-$Z_6$ are each independently selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein $R_1$ and/or $R_2$ are substituted or non-substituted.

9. A method of synthesis, the method comprising the steps of:
combining a halogenation agent with a compound represented by structural Formula (I) or a pharmaceutically acceptable salt thereof:

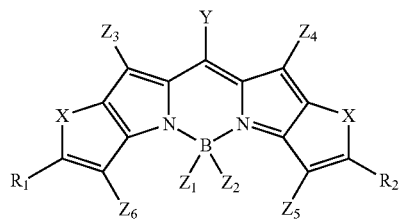

Formula (I)

wherein:
Y represents $CF_3$, $CCl_3$, $CBr_3$, $CI_3$ or $CH_3$;
X represents O, S, Se, or Te;
$Z_1$ and $Z_2$ are each independently selected from the group consisting of a halogen, alkyl, alkenyl, alkynyl, alkoxy, aryl, heteroaryl, heteroarylalkyl, and heteroarylalkoxy, wherein the heteroatom is O, S, or N;
$Z_3$, $Z_4$, $Z_5$, and $Z_6$ are hydrogen; and
$R_1$ and $R_2$ are each independently selected from the group consisting of an alkyl, alkenyl, alkynyl, alkoxy, aryl, haloaryl, haloheteroaryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein the $R_1$ and $R_2$ groups are substituted or non-substituted; and
reacting the compound with the halogenation agent under conditions which cause substitution of the hydrogen of at least two of $Z_3$-$Z_6$ with a halogen selected from the group consisting of Cl, F, Br, and I, thereby forming a halogenated compound wherein at least two of $Z_3$-$Z_6$ are each a halogen.

10. The method of claim 9, wherein each of $R_1$ and $R_2$ is each independently selected from at least one of the following structures:

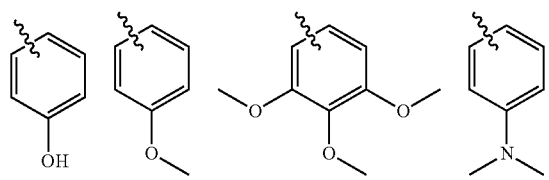

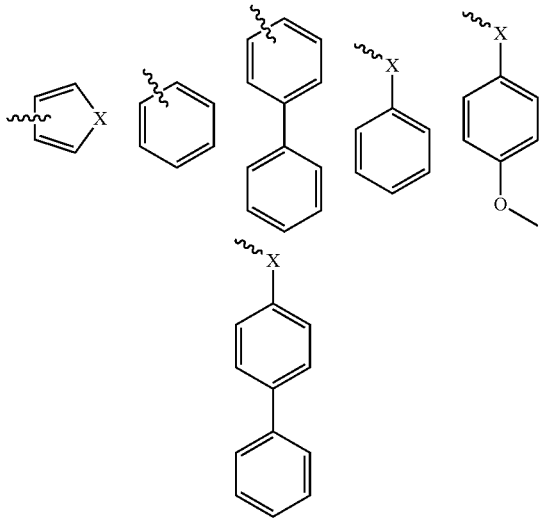

wherein X represents NH, O, or S.

11. A method of synthesis, the method comprising the steps of:
combining a halogenated compound with a reactant able to provide a modifying group, wherein the halogenated compound is represented by structural Formula (I) or a pharmaceutically acceptable salt thereof:

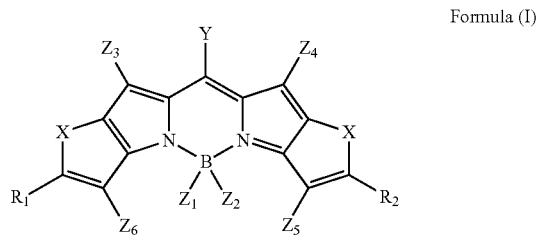

Formula (I)

wherein:
Y represents $CF_3$, $CCl_3$, $CBr_3$, $CI_3$, or $CH_3$;
X represents O, S, Se, or Te;
$Z_1$ and $Z_2$ are each independently selected from the group consisting of a halogen, alkyl, alkenyl, alkynyl, alkoxy, aryl, heteroaryl, heteroarylalkyl, and heteroarylalkoxy, wherein the heteroatom is O, S, or N;
at least two of $Z_3$, $Z_4$, $Z_5$, and $Z_6$ are a halogen selected from the group consisting of Cl, F, Br, and I, and the remainder of $Z_3$-$Z_6$ are hydrogen; and
$R_1$ and $R_2$ are each independently selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein the modifying group is substituted or non-substituted; and reacting the halogenated compound with the reactant under conditions suitable for causing substitution of each of the halogens of the at least two of $Z_3$-$Z_6$ with the modifying group from the reactant, thereby forming a derivative of said halogenated compound, wherein the modifying group is selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein the modifying group is substituted or non-substituted.

12. The method of claim 11, wherein the modifying group is at least one of the following structures:

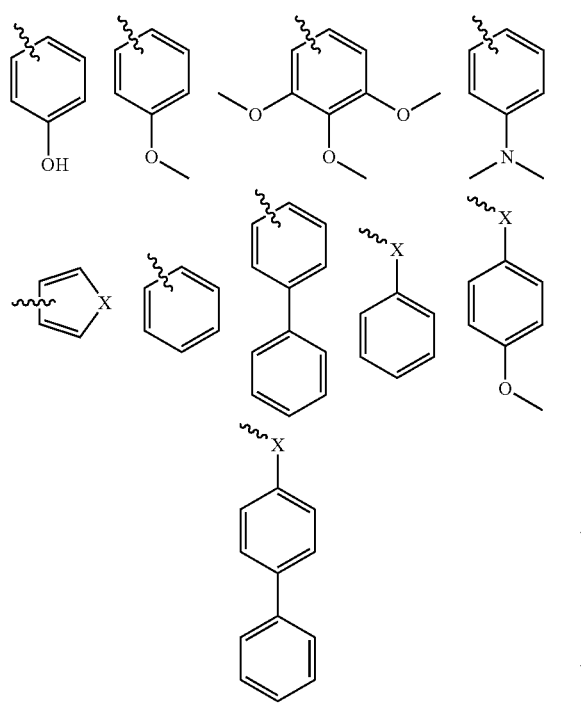

wherein X represents NH, O, or S.

13. A method of synthesis, the method comprising the steps of:
combining a compound with a reactant able to provide a modifying group, wherein the compound is represented by structural Formula (III) or a pharmaceutically acceptable salt thereof:

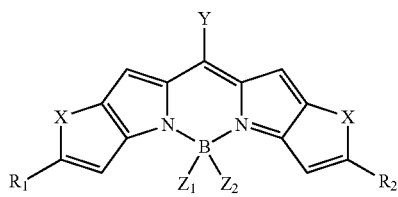

Formula (III)

wherein:
Y represents $CF_3$, $CCl_3$, $CBr_3$, $CI_3$ or $CH_3$;
X represents O, S, Se, or Te;
$Z_1$ and $Z_2$ each independently represents F, Cl, Br, or I; and
$R_1$ and $R_2$ each independently represents F, Cl, Br, or I; and reacting said compound with the reactant under conditions suitable for causing substitution of the $R_1$ and $R_2$ of said compound with the modifying group from the reactant, thereby forming a derivative of said compound, wherein the modifying group is selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein the modifying group is substituted or non-substituted.

14. The method of claim 13, wherein the modifying group is at least one of the following structures:

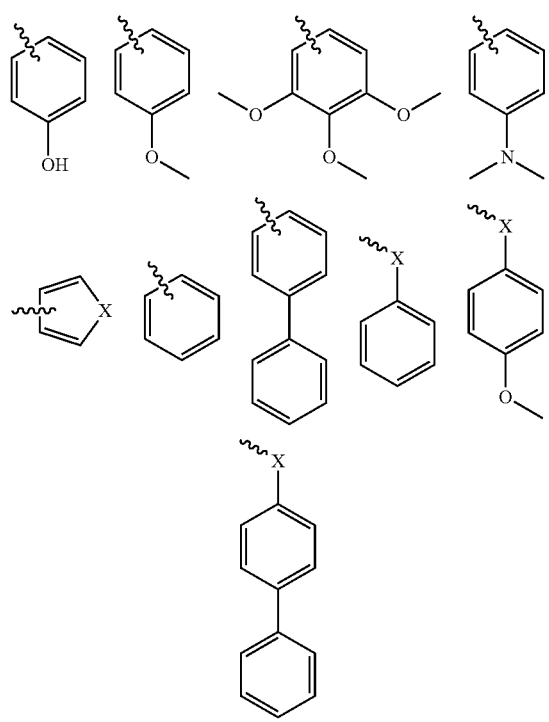

wherein X represents NH, O, or S.

15. The method of synthesis of claim 13,
wherein in the step of providing the compound, Y represents $CF_3$, X represents S, $Z_1$ and $Z_2$ each represents F, and $R_1$ and $R_2$ each represents Br.

16. The method of claim 15, wherein the modifying group is at least one of the following structures:

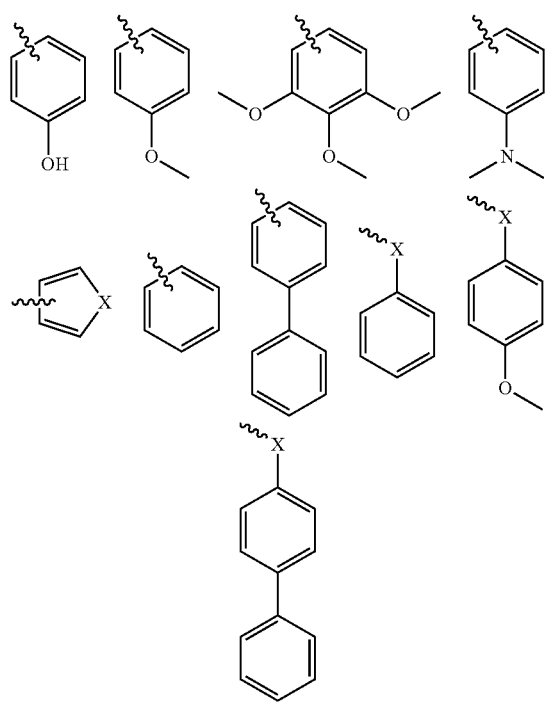

wherein X represents NH, O, or S.

17. A compound represented by structural Formula (I) or a pharmaceutically acceptable salt thereof:

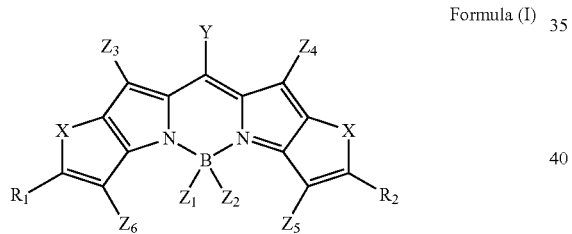

Formula (I)

wherein:
Y represents $CF_3$, $CCl_3$, $CBr_3$, $CI_3$, or $CH_3$;
X represents O, S, Se, or Te;
$Z_1$ and $Z_2$ are each independently selected from the group consisting of a halogen, alkyl, alkenyl, alkynyl, alkoxy, aryl, heteroaryl, heteroarylalkyl, and heteroarylalkoxy, wherein the heteroatom is O, S, or N;
$Z_3$, $Z_4$, $Z_5$, and $Z_6$ are each independently selected from the group consisting of hydrogen, a halogen, alkyl, alkenyl, alkynyl, alkoxy, aryl, heteroalkyl, heteroalkoxy, heteroaryl, heteroarylalkyl, heteroarylalkoxy, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein at least two of $Z_3$, $Z_4$, $Z_5$, and $Z_6$ are not hydrogen; and
$R_1$ and $R_2$ are each independently selected from the group consisting of a halogen, alkyl, alkenyl, alkynyl, alkoxy, aryl, haloaryl, haloheteroaryl, heteroalkyl, het-eroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein the $R_1$ and $R_2$ groups are substituted or non-substituted.

18. The compound of claim 17, wherein each of $R_1$ and $R_2$ is independently selected from at least one of the following structures:

wherein X represents NH, O, or S.

19. The compound of claim 17, wherein:
at least two of $Z_3$-$Z_6$ comprise a halogen selected from the group consisting of Cl, F, Br, and I; and
$R_1$ and $R_2$ are each independently selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein $R_1$ and/or $R_2$ are substituted or non-substituted.

20. The compound of claim 17, wherein $R_1$ and $R_2$ and at least two of $Z_3$-$Z_6$ are each independently selected from the group consisting of alkyl, alkenyl, alkynyl, alkoxy, aryl, heteroalkyl, heteroalkoxy, heteroaryl, alkylaryl, alkoxyaryl, alkenylaryl, alkylheteroaryl, alkoxyheteroaryl, alkenylheteroaryl, haloaryl, haloheteroaryl, heteroatom-aryl, heteroatom-heteroaryl, biaryl, biheteroaryl, aryl-heteroaryl, biaryloxy, biheteroaryloxy, heteroaryl-aryloxy, aryl-heteroaryloxy, heteroatom-heteroaryl-aryloxy, heteroatom-aryl-heteroaryloxy, diarylether, and diheteroarylether, wherein the heteroatom is O, S, or N, and wherein $R_1$ and/or $R_2$ are substituted or non-substituted.

* * * * *

UNITED STATES PATENT AND TRADEMARK OFFICE
CERTIFICATE OF CORRECTION

PATENT NO. : 9,611,281 B2
APPLICATION NO. : 14/562323
DATED : April 4, 2017
INVENTOR(S) : Youngjae You, Samuel Awuah and Ryan Watley It is certified that error appears in the above-identified patent and that said Letters Patent is hereby corrected as shown below:

In the Specification

Column 8, Lines 1 - 11: Delete Formula (I) in its entirety and replace with the following:

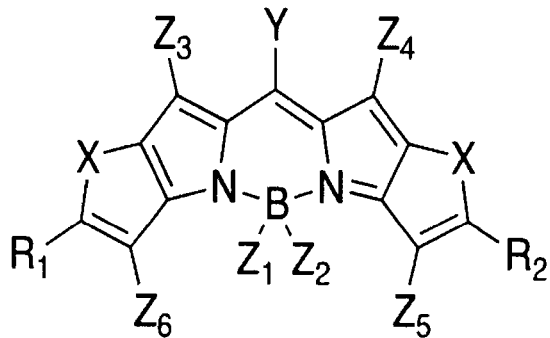

Formula (I).

Column 8, Lines 46 - 55: Delete Formula (II) in its entirety and replace with the following:

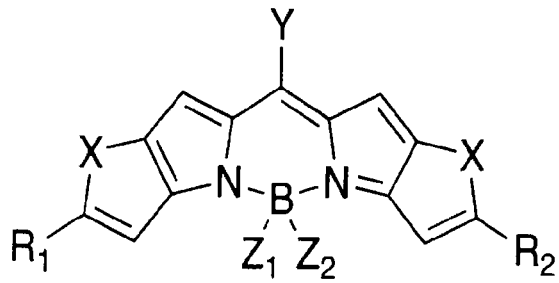

Formula (II).

Signed and Sealed this
Fourth Day of July, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,611,281 B2

Column 9, Lines 7 - 18: Delete Formula (III) in its entirety and replace with the following:

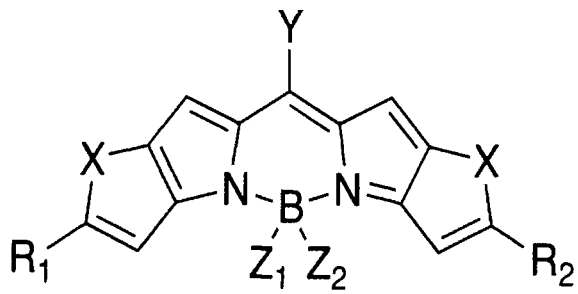

-- Formula (III). --

Column 9, Lines 30 - 40: Delete Formula (IV) in its entirety and replace with the following:

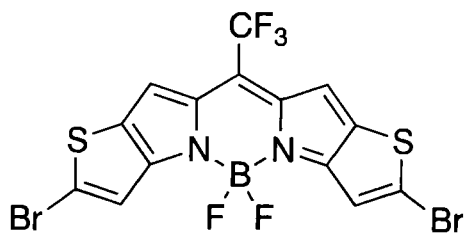

-- Formula (IV). --

Column 15, Line 26: Delete "246.0812." and replace with -- 246.0812; --

Column 15, Line 28: Before "-trifluoromethyl" delete "1" and replace with -- 11 --

Column 15, Line 48: Delete "529.8200." and replace with -- 529.8200; --

Column 17, Line 22: Delete "556.0510." and replace with -- 556.0510; --

Column 17, Line 42: Delete "584.0823." and replace with -- 584.0823; --

Column 17, Line 62: Delete "535.9740." and replace with -- 535.9740; --

Column 18, Line 14: Delete "704.1245." and replace with -- 704.1245, --

Column 18, Line 33: Delete "610.1456." and replace with -- 610.1456, --

Column 19, Line 8: Delete "576.0925." and replace with -- 576.0925; --

Column 19, Line 26: Delete "636.1136." and replace with -- 636.1136; --

Column 19, Line 51: Before "-trifluoromethyl" delete "1" and replace with -- 11 --

CERTIFICATE OF CORRECTION (continued)
U.S. Pat. No. 9,611,281 B2

Column 19, Line 66: Delete "524.0612." and replace with -- 524.0612; --

Column 20, Line 38: Delete "588.0053." and replace with -- 588.0053; --

Column 20, Line 54: Delete "616.0721." and replace with -- 616.0721; --

Column 21, Line 3: Delete "708.1136." and replace with -- 708.1136; --

Column 24, Line 63: Delete "229.0561." and replace with -- 229.0561; --

Column 25, Line 23: Delete "650.1317." and replace with -- 650.1317; --

Column 26, Line 1: Delete "(nm/z):" and replace with -- ($m/z$): --

Column 26, Line 2: Delete "728.1245." and replace with -- 728.1245; --

Column 26, Line 19: Delete "885.9435." and replace with -- 885.9435; --

Column 26, Line 32: Delete "(nm/z):" and replace with -- ($m/z$): --

Column 26, Line 32: Delete "829.8809." and replace with -- 829.8809; --

In the Claims

Column 34, Lines 25 - 32: Delete Formula (IV) in its entirety and replace with the following:

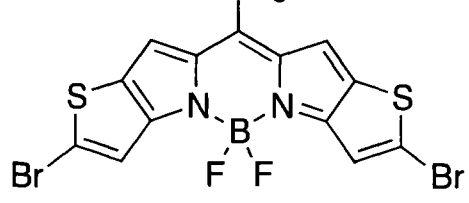

-- Formula (IV). --